(12) United States Patent
Brace et al.

(10) Patent No.: US 12,029,457 B2
(45) Date of Patent: Jul. 9, 2024

(54) BONE FIXATION SYSTEM

(71) Applicant: DePuy Synthes Products, Inc., Raynham, MA (US)

(72) Inventors: Michael Brace, Lansdale, PA (US); William N. Woodburn, Sr., Mickleton, NJ (US); Carl Peter Cornelius, Munich (DE)

(73) Assignee: DePuy Synthes Products, Inc., Raynham, MA (US)

( * ) Notice: Subject to any disclaimer, the term of this patent is extended or adjusted under 35 U.S.C. 154(b) by 454 days.

(21) Appl. No.: 17/209,573

(22) Filed: Mar. 23, 2021

(65) Prior Publication Data
US 2021/0204990 A1 Jul. 8, 2021

Related U.S. Application Data

(63) Continuation of application No. 15/677,101, filed on Aug. 15, 2017, now Pat. No. 10,980,584.

(60) Provisional application No. 62/375,781, filed on Aug. 16, 2016.

(51) Int. Cl.
*A61B 17/80* (2006.01)
*A61B 17/70* (2006.01)
*A61B 17/86* (2006.01)

(52) U.S. Cl.
CPC ...... *A61B 17/8057* (2013.01); *A61B 17/7059* (2013.01); *A61B 17/8047* (2013.01); *A61B 17/8085* (2013.01); *A61B 17/8071* (2013.01); *A61B 17/863* (2013.01)

(58) Field of Classification Search
CPC ............ A61B 17/8057; A61B 17/7059; A61B 17/8047; A61B 17/8085; A61B 17/8071; A61B 17/863
See application file for complete search history.

(56) References Cited

U.S. PATENT DOCUMENTS

| | | |
|---|---|---|
| 870,242 A | 11/1907 | Meech |
| 1,182,980 A | 5/1916 | Converse |
| 2,035,308 A | 3/1936 | Paul |
| 3,488,779 A | 1/1970 | Christensen |
| 3,805,302 A | 4/1974 | Mathys |
| 4,429,690 A | 2/1984 | Angelino-Pievani |
| 5,053,036 A | 10/1991 | Perren et al. |
| 5,704,936 A | 1/1998 | Mazel |
| 5,713,900 A | 2/1998 | Benzel et al. |
| 5,975,904 A | 11/1999 | Spiegel |
| 6,030,389 A | 2/2000 | Wagner et al. |

(Continued)

FOREIGN PATENT DOCUMENTS

| | | |
|---|---|---|
| CN | 1700890 A | 11/2005 |
| CN | 1985770 A | 6/2007 |

(Continued)

OTHER PUBLICATIONS

U.S. Appl. No. 15/677,101, filed Aug. 15, 2017.

*Primary Examiner* — Sameh R Boles
(74) *Attorney, Agent, or Firm* — BakerHostetler

(57) ABSTRACT

A modular bone fixation linkage includes a plurality of interconnected links that can angulate with respect to an adjacent one of the links in-plane or out-of-plane. The links can further include fixation holes that are configured to receive fixation members that secure the links to an underlying anatomical structure.

20 Claims, 11 Drawing Sheets

(56) References Cited

U.S. PATENT DOCUMENTS

| | | |
|---|---|---|
| 6,053,921 A | 4/2000 | Wagner et al. |
| 6,060,641 A | 5/2000 | Manolidis |
| 6,136,002 A | 10/2000 | Shih et al. |
| 6,730,091 B1 | 5/2004 | Pfefferle et al. |
| 6,749,612 B1 | 6/2004 | Conchy et al. |
| 7,090,676 B2 | 8/2006 | Huebner et al. |
| 7,201,753 B2 | 4/2007 | Schlaapfer et al. |
| 7,935,126 B2 | 5/2011 | Orbay et al. |
| 7,988,691 B2 | 8/2011 | Schulze et al. |
| 8,221,472 B2 | 7/2012 | Peterson et al. |
| 8,343,154 B2 | 1/2013 | Long et al. |
| 8,343,196 B2 | 1/2013 | Schneider |
| 8,506,605 B2 | 8/2013 | Bickley et al. |
| 8,795,277 B2 | 8/2014 | Leuenberger et al. |
| 9,101,428 B2 | 8/2015 | Long et al. |
| 10,188,439 B2 | 1/2019 | Woodburn et al. |
| 2001/0034521 A1 | 10/2001 | Bailey et al. |
| 2002/0183755 A1 | 12/2002 | Michelson |
| 2002/0183756 A1 | 12/2002 | Michelson |
| 2004/0039388 A1 | 2/2004 | Biedermann et al. |
| 2004/0092930 A1 | 5/2004 | Petit et al. |
| 2004/0102778 A1 | 5/2004 | Huebner et al. |
| 2004/0116931 A1 | 6/2004 | Carlson |
| 2005/0027298 A1 | 2/2005 | Michelson |
| 2005/0154388 A1 | 7/2005 | Roussouly et al. |
| 2005/0154392 A1 | 7/2005 | Medoff et al. |
| 2005/0277920 A1 | 12/2005 | Slivka et al. |
| 2006/0149228 A1 | 7/2006 | Schlapfer et al. |
| 2007/0123881 A1 | 5/2007 | Ralph et al. |
| 2007/0233085 A1 | 10/2007 | Biedermann et al. |
| 2007/0293863 A1 | 12/2007 | Reimels et al. |
| 2008/0097432 A1 | 4/2008 | Schulze |
| 2008/0097445 A1 | 4/2008 | Weinstein |
| 2008/0140130 A1 | 6/2008 | Chan et al. |
| 2008/0234676 A1 | 9/2008 | Schulze et al. |
| 2009/0082813 A1 | 3/2009 | Long et al. |
| 2010/0121328 A1 | 5/2010 | Reitzig et al. |
| 2010/0179552 A1 | 7/2010 | Wolter |
| 2010/0274248 A1 | 10/2010 | Overes et al. |
| 2010/0305569 A1 | 12/2010 | Leuenberger et al. |
| 2010/0324558 A1 | 12/2010 | Bickley et al. |
| 2011/0218534 A1 | 9/2011 | Prandi et al. |
| 2011/0270316 A1 | 11/2011 | Piehl |
| 2012/0184995 A1 | 7/2012 | Miller |
| 2015/0018829 A1* | 1/2015 | Woodburn, Sr. ... A61B 17/8057 606/71 |

FOREIGN PATENT DOCUMENTS

| | | |
|---|---|---|
| CN | 1985771 A | 6/2007 |
| CN | 101594834 A | 12/2009 |
| CN | 101808589 A | 8/2010 |
| CN | 105517501 A | 4/2016 |
| DE | 202007001585 U1 | 5/2007 |
| EP | 1861030 A2 | 12/2007 |
| JP | 07-501735 | 2/1995 |
| JP | 2002-527137 A | 8/2002 |
| JP | 2003-522589 A | 7/2003 |
| JP | 2004-530482 A | 10/2004 |
| JP | 2007-517584 A | 7/2007 |
| JP | 2009-513245 A | 4/2009 |
| JP | 2010-528706 | 8/2010 |
| JP | 2012-524631 A | 10/2012 |
| WO | 02/76315 A1 | 10/2002 |
| WO | 2005/069752 A2 | 8/2005 |
| WO | 2006/102222 A2 | 9/2006 |
| WO | 2007/050276 A2 | 5/2007 |
| WO | 2008/150501 | 12/2008 |
| WO | 2009/049161 A2 | 4/2009 |
| WO | 2015/006188 A1 | 1/2015 |

* cited by examiner

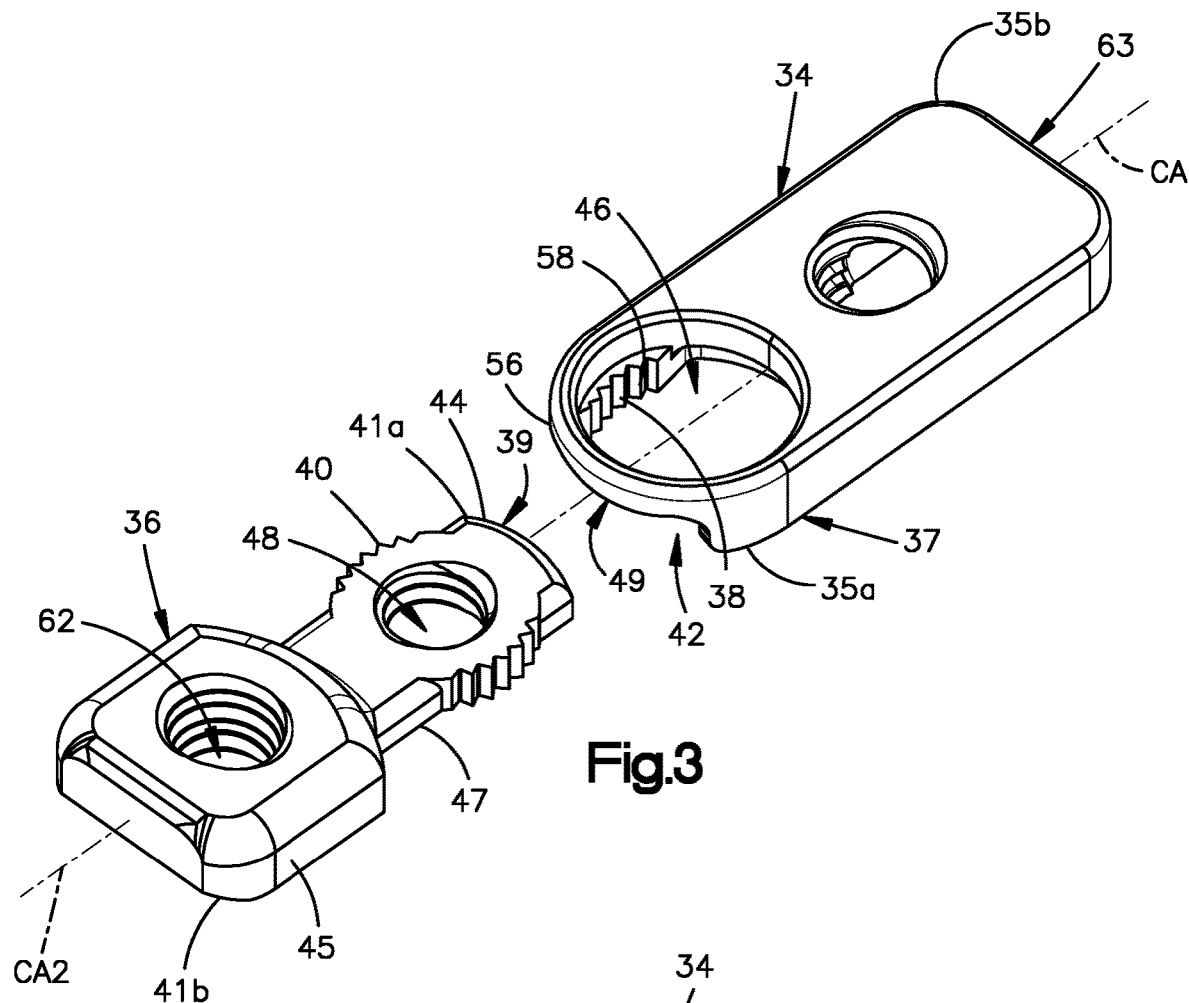
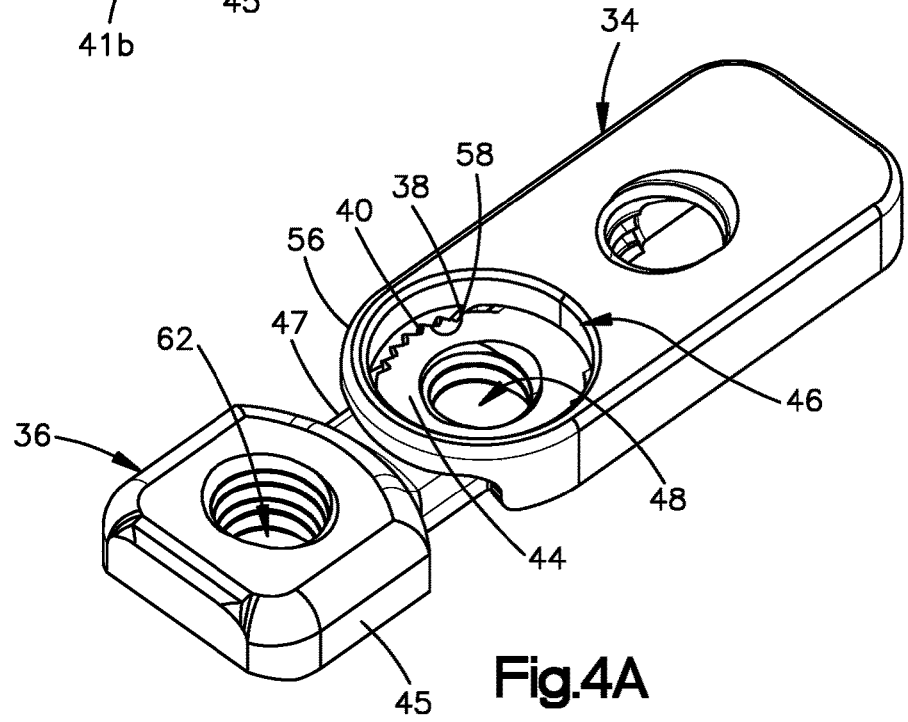

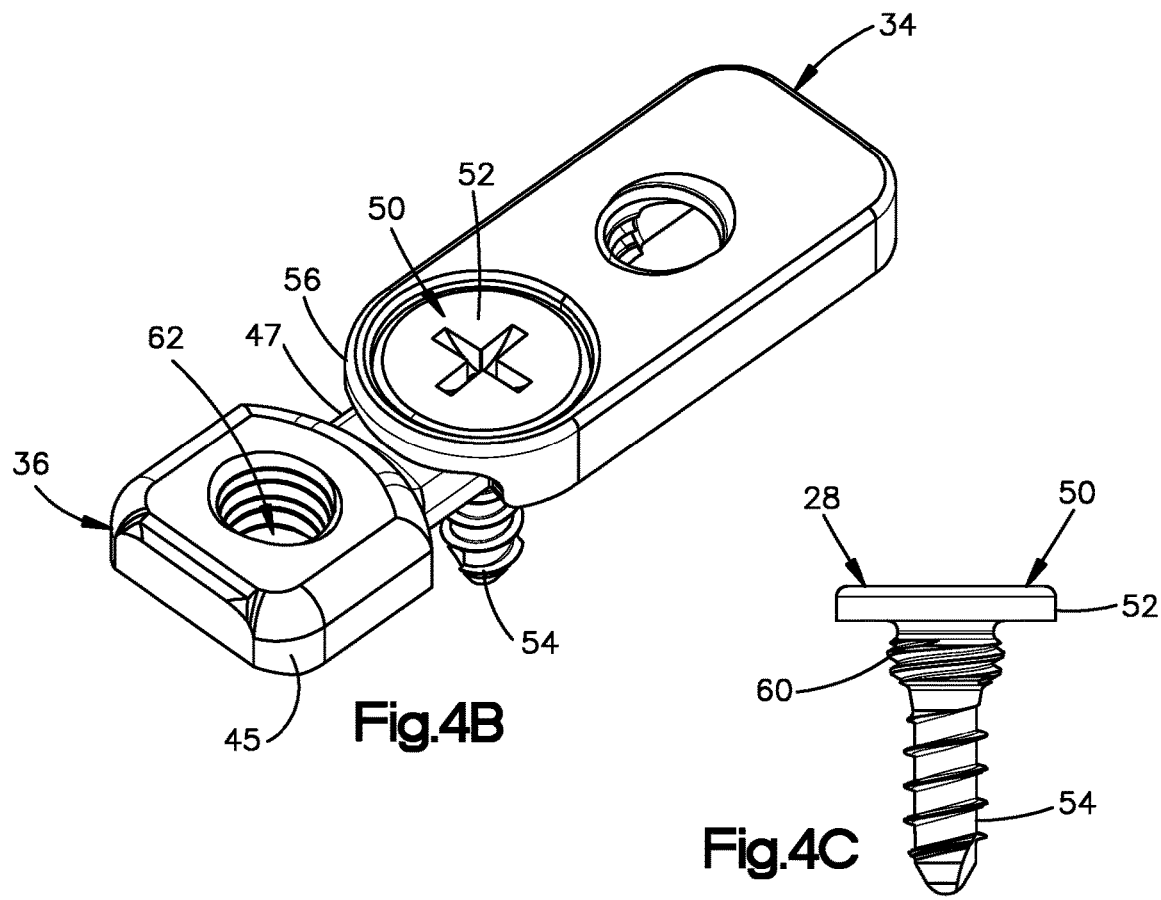
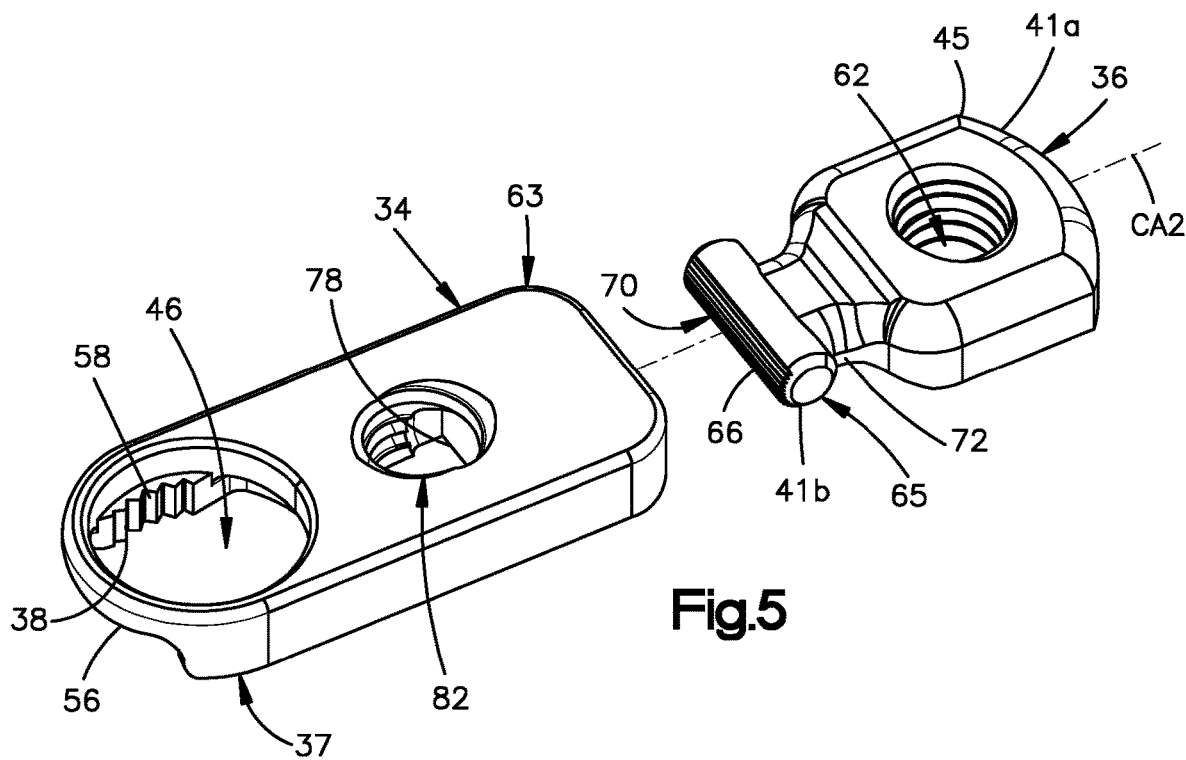

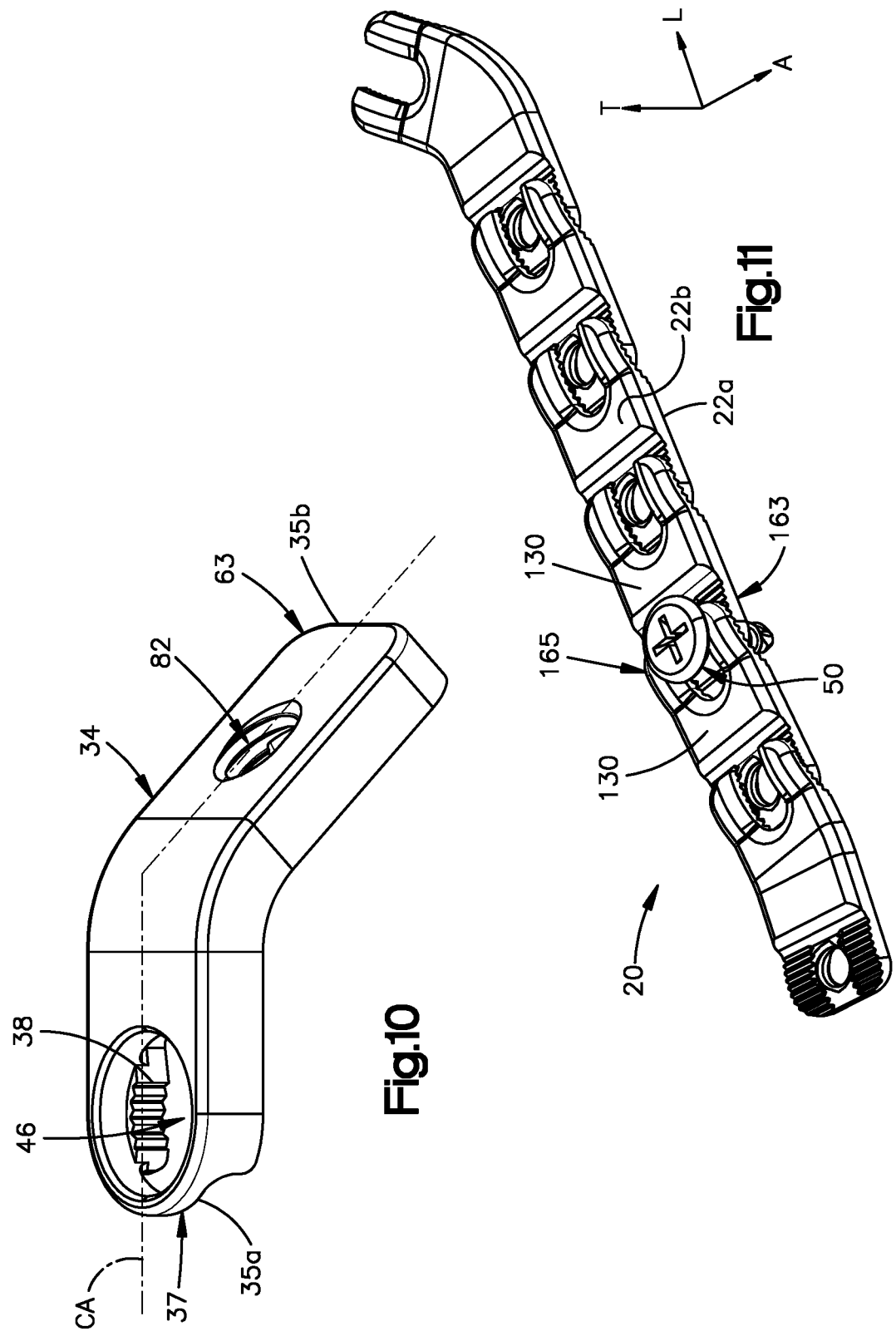

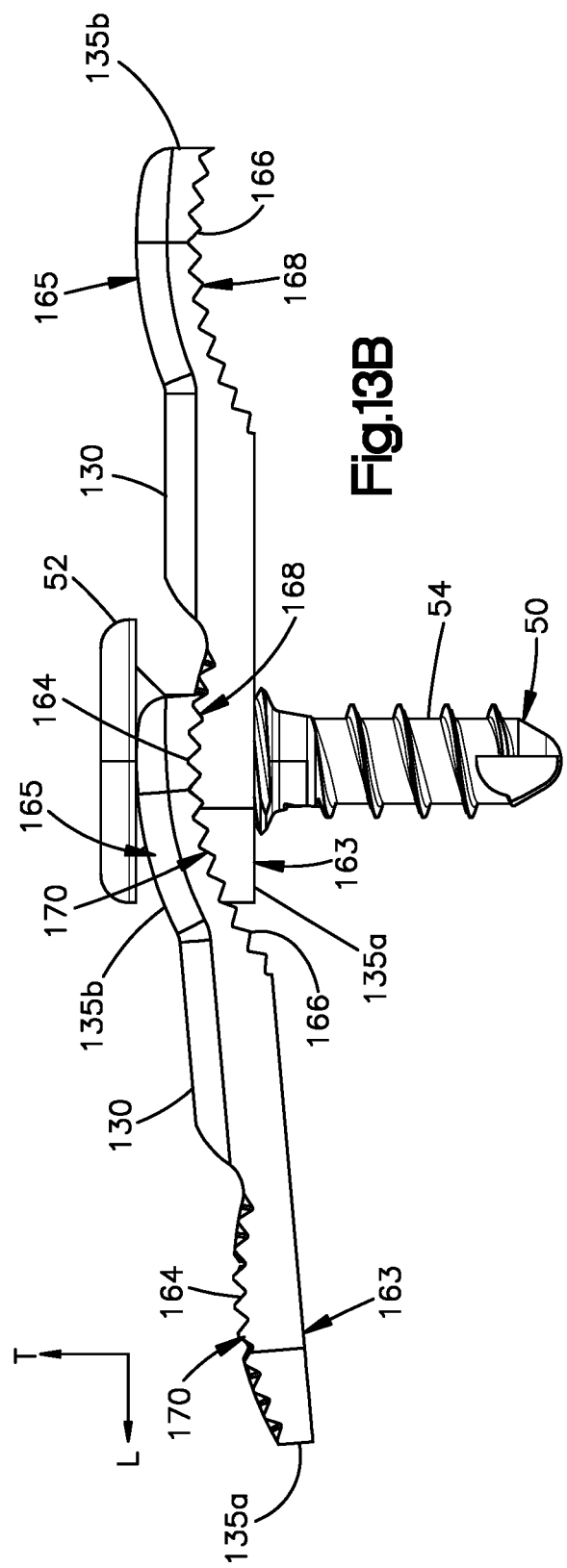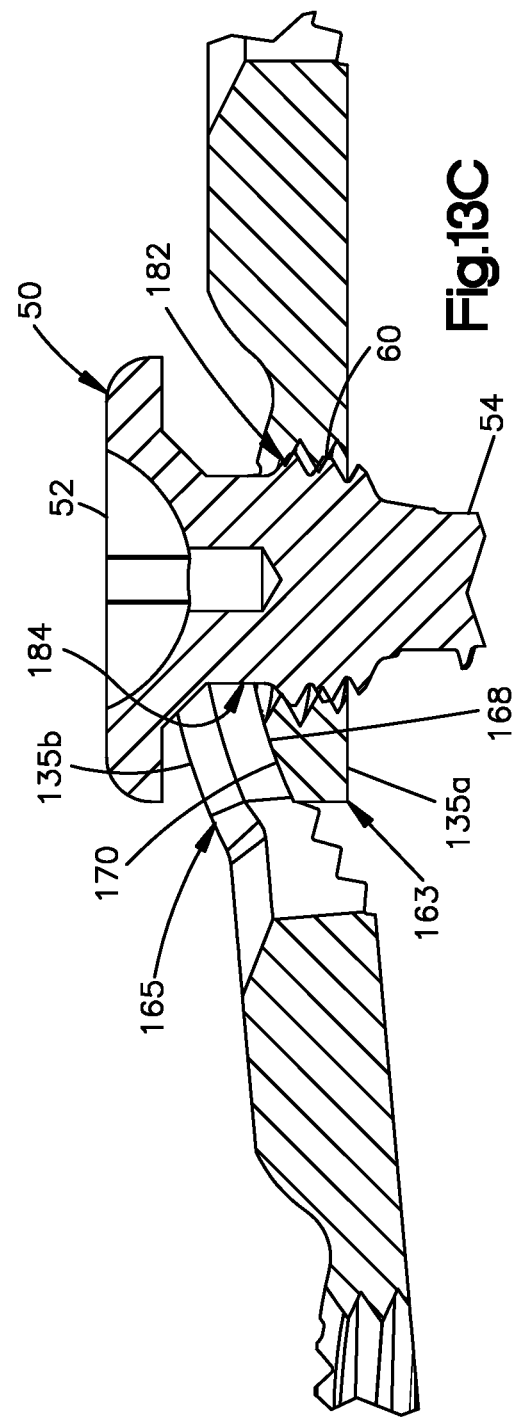

BONE FIXATION SYSTEM

CROSS-REFERENCE TO RELATED APPLICATIONS

This is a continuation of U.S. patent application Ser. No. 15/677,101 filed Aug. 15, 2017, which claims the benefit of U.S. Patent Application Ser. No. 62/375,781 filed Aug. 16, 2016, the disclosure of each of which is hereby incorporated by reference as if set forth in its entirety herein.

BACKGROUND

This disclosure relates generally to bone fixation implants, and in particular relates to an adaptable bone fixation implant that can be readily shaped to repair or replace a particular bone structure of a patient.

When bones are damaged through trauma, disease, distraction osteogenesis, or orthognathic surgery, bone fixation implants are commonly used to provide anatomical reduction of bone fragments, to maintain their position, and to ensure union in the desired position. Thus, bone fixation implants are typically designed to achieve proper anatomic fit and function. Additionally, because bone fixation implants often support bones that withstand significant mechanical stress in their anatomic function, implants are often composed of strong and rigid materials. However, it is particularly difficult to fashion rigid materials to a particular patient's bone contour.

As one example, achieving the proper shape and fit of a bone fixation implant is of particular emphasis in mandibular reconstruction. An improper fit of a mandibular fixation implant may result in disruption of the normal jaw function or alteration of the occlusion, which can cause discomfort for a patient. Additionally, it is desirable for mandibular fixation implants to be strong and rigid to provide a proper occlusion and withstand related mechanical stresses.

SUMMARY

In accordance with one embodiment, a bone fixation linkage defines an inner end configured to face a bone to which the bone fixation linkage is configured to be attached, and an outer end opposite the inner end. The fixation linkage includes at least a first link of the plurality of interconnected links including a plurality of first locking ribs spaced from each other along a plane, and at least a second link of the plurality of interconnected links including a plurality of second locking ribs. At least one of the second locking ribs is configured to mate with at least one of the first locking ribs so as to lock the first link to the second link The at least one first locking rib can prevent the second link from rotating with respect to the first link about an axis of rotation that is normal to the plane when the at least one second locking rib is mated with the at least one first locking rib.

BRIEF DESCRIPTION OF THE DRAWINGS

The foregoing summary, as well as the following detailed description, is better understood when read in conjunction with the appended drawings. For the purpose of illustrating the reconstruction device and related method thereof, there is shown in the drawings exemplary embodiments, in which like reference numerals correspond to like reference numerals throughout. The reconstruction device and related methods are not limited to the specific embodiments and methods disclosed, and reference is made to the claims for that purpose.

FIG. 3 is a perspective view of first and second links of the bone fixation linkage illustrated in FIG. 2, the first and second links having respective mating in-plane attachment ends;

FIG. 4A is a perspective view of the first and second links illustrated in FIG. 3, shown attached to each other;

FIG. 4B is a perspective view of the first and second links illustrated in FIG. 4B, shown locked to each other with a fixation member;

FIG. 4C is a side elevation view of the fixation member illustrated in FIG. 4B;

FIG. 5 is a perspective view of first and second links of the plurality of links illustrated in FIG. 2, the first and second links having respective mating out-of-plane attachment ends;

FIG. 10 is a perspective view of one of the first links of the linkage illustrated in FIG. 2, shown having an out-of-plane elbow in accordance with an alternative embodiment.

FIG. 11 is a perspective view of a bone fixation system constructed in accordance with an alternative embodiment, the bone fixation system including a bone fixation linkage and a plurality of fixation members;

FIG. 13B is a side elevation view of the first and second ones of the bone fixation links shown locked to each other with a fixation member;

FIG. 13C is a sectional side elevation view of the first and second ones of the bone fixation links illustrated in FIG. 13B;

DETAILED DESCRIPTION

Figure 1:
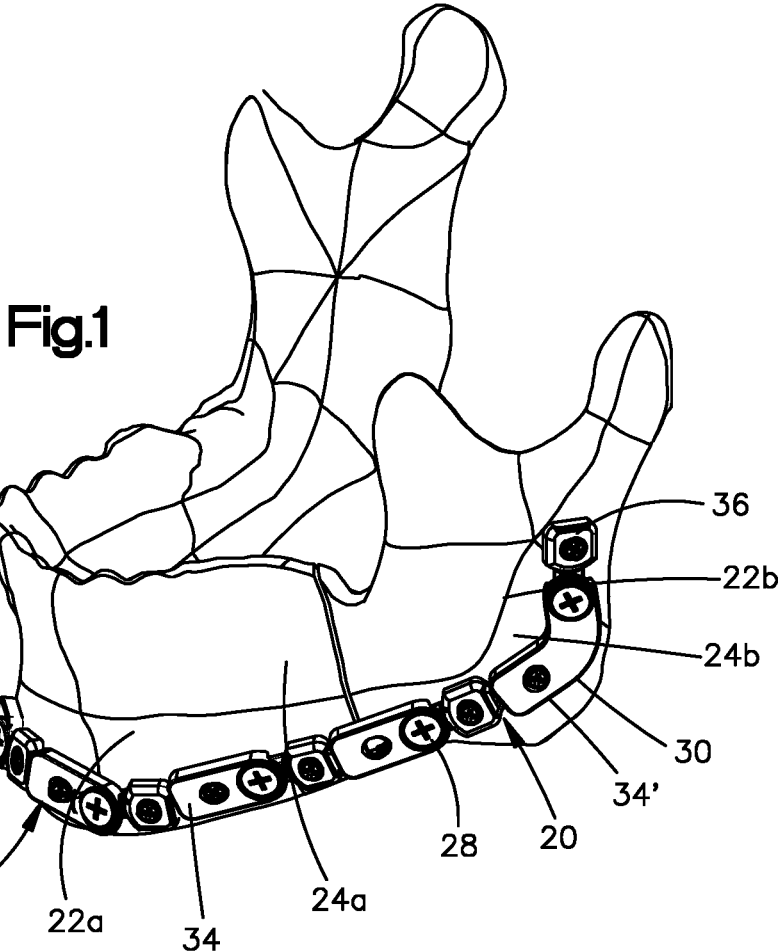
FIG. 1 is a perspective view of a bone fixation system including a bone fixation linkage and a plurality of bone anchors, shown implanted onto a target bone in accordance with one embodiment.
Figure 2:
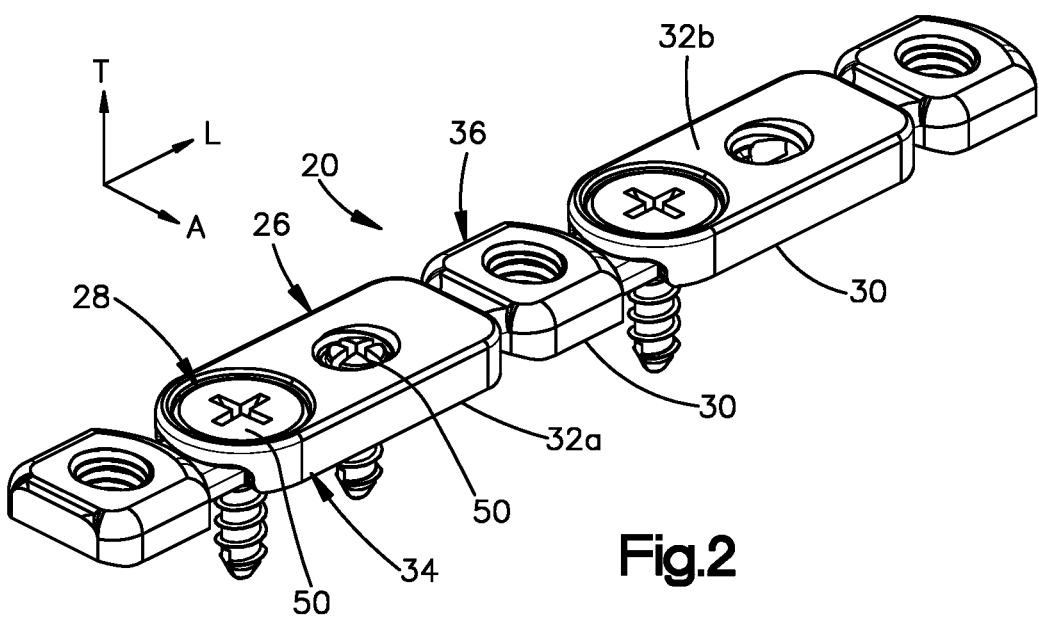
FIG. 2 is a perspective view of a plurality of links of the bone fixation linkage illustrated in FIG. 1, the links including a plurality of first links and a plurality of second links alternatingly arranged with each other and interconnected to each other.
Figure 6A:
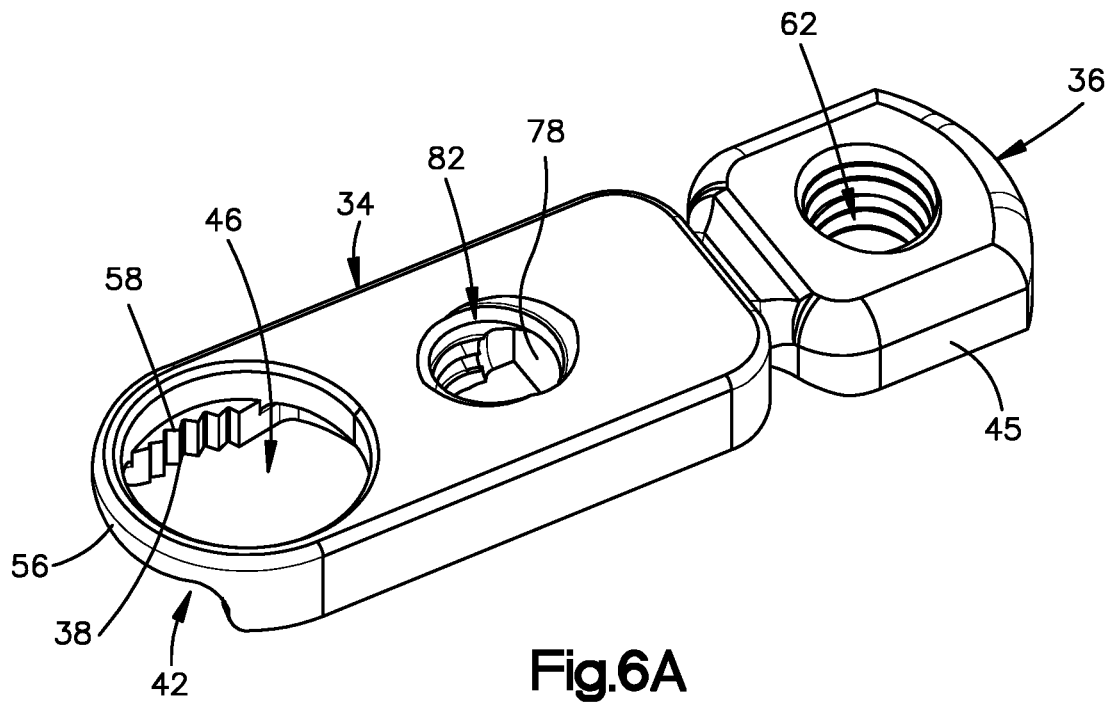
FIG. 6A is a perspective view of the first and second links illustrated in FIG. 5, shown attached to each other.
Figure 6B:
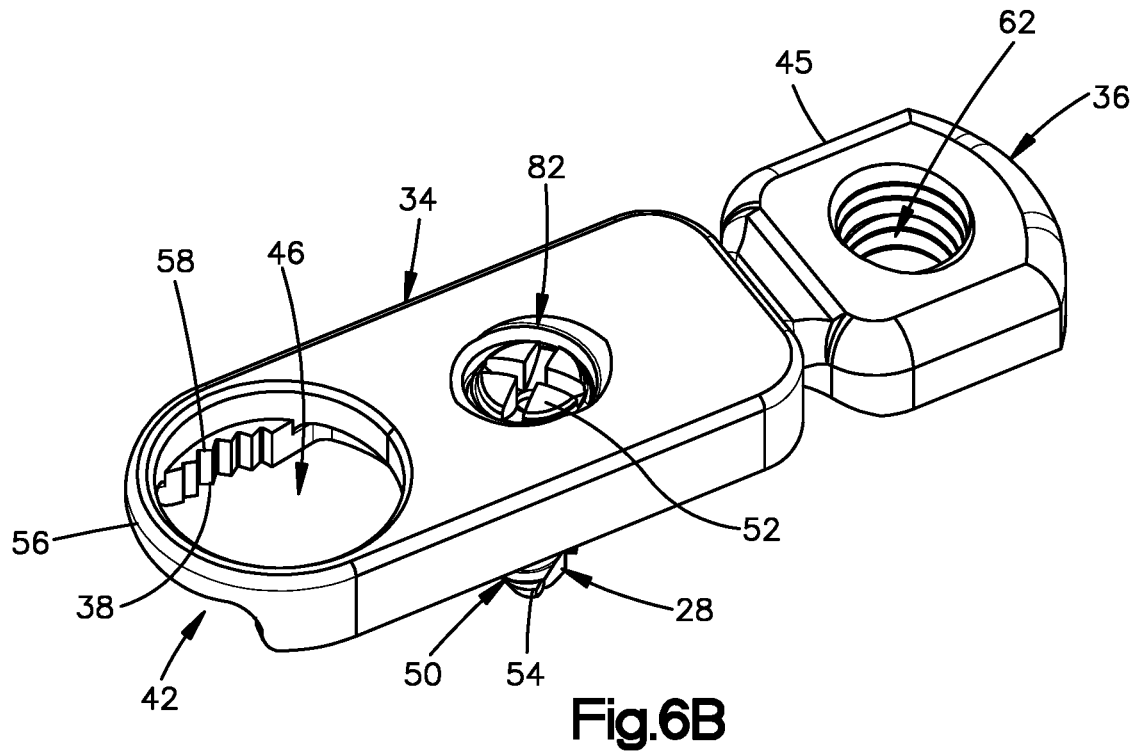
FIG. 6B is a perspective view of the first and second links illustrated in FIG. 6B, shown locked to each other with a fixation member.
Figure 7A:
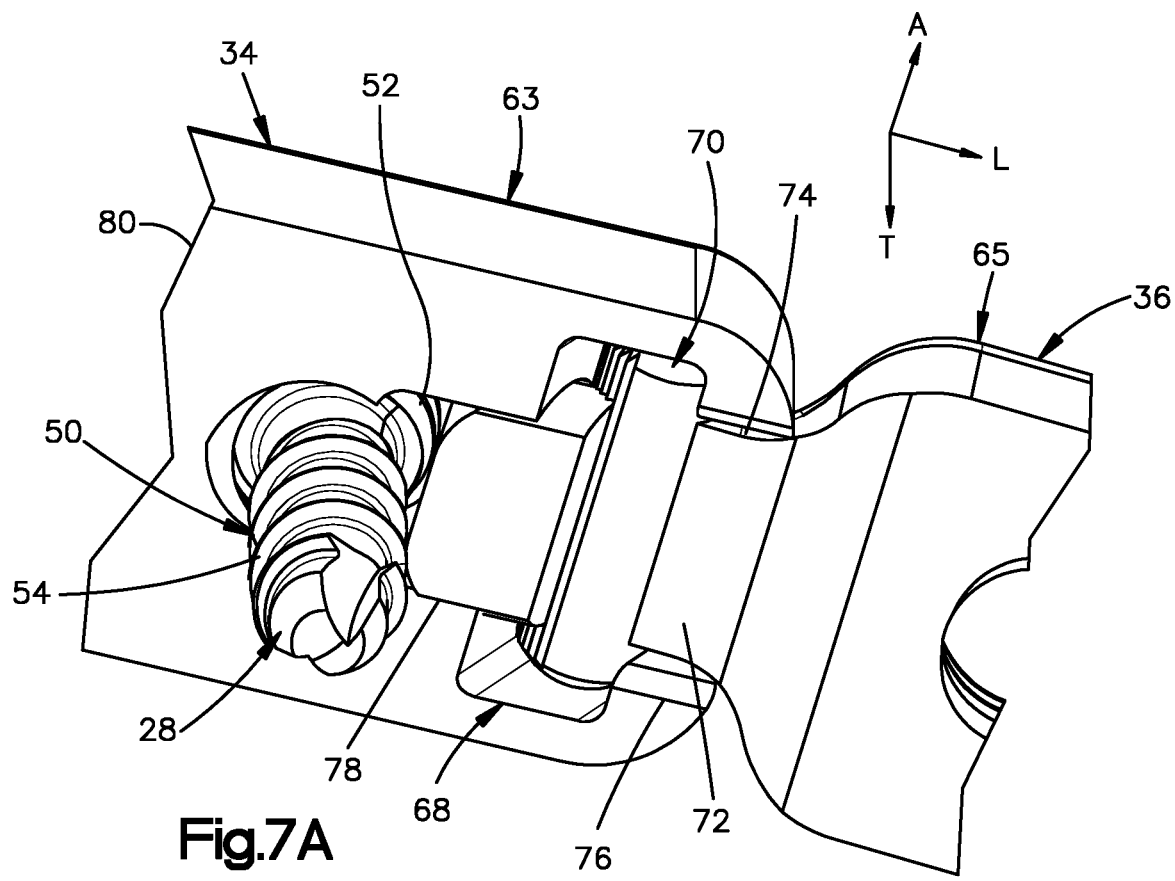
FIG. 7A is another perspective view of the first and second links illustrated in FIG. 6B, shown locked to each other.
Figure 7B:
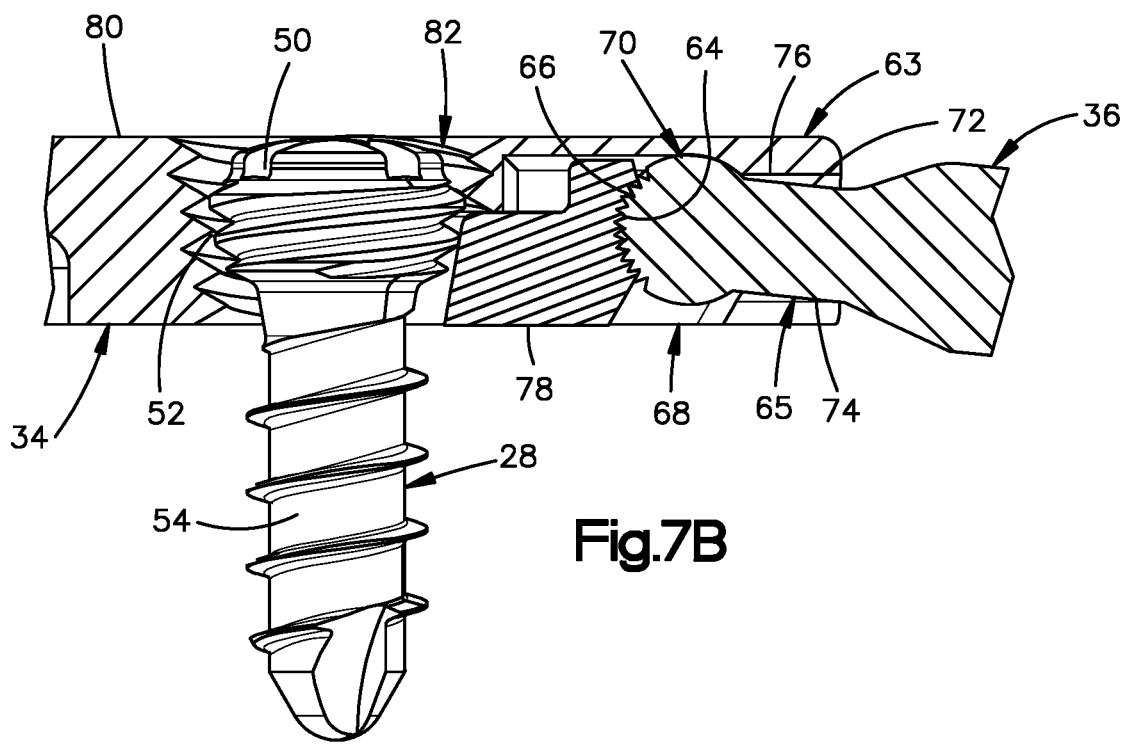
FIG. 7B is a sectional side elevation view of the first and second links illustrated in FIG. 7A, shown locked to each other.

Referring to FIGS. 1-2B, a bone fixation system 20 is configured to be implanted onto bone so as to stabilize a first anatomical structure 22a with respect to at least second anatomical structure 22b so as to promote bone healing or bridging of a bone gap. The bone fixation system 20 can include a bone fixation linkage 26 that is configured to be attached to each of the first and second anatomical structures 22a and 22b, and a plurality of fixation members 50 that are configured to fix the bone fixation linkage 26 to positionally fix the anatomical structures 22a and 22b to fix the anatomical structures 22a and 22b relative to each other. The fixation members 28 can include bone fixation members 28. The bone fixation linkage 26 includes a plurality of interconnected links 30 that are configured to be attached to each other and to the underlying anatomical structures. As will be appreciated from the description below, the links 30 are configured to be manipulated relative to each other so as to fit against the underlying anatomical structure, and adjacent ones of the links 30 are configured to be locked to each other so as to positionally fix the bone fixation linkage 26.

The first anatomical structure 22a can be configured as a bone or bone fragment 24a as illustrated. The term "bone" can be used to refer collectively to bone or a bone fragment. The second anatomical structure 22b can be configured as another bone fragment 24b, separated by a bone gap G, for instance when a bone is fractured, or when an osteotomy is performed on a bone 24. The second anatomical structure 22b can also be another bone fragment when a bone is resectioned so as to define a bone gap that separates the first and second bone fragments. Alternatively or additionally, the bone fixation system 20 is configured to stabilize the first anatomical structure with respect to a bone implant, which can be an artificial implant or a bone graft. In one example, the bone graft can be placed in the bone gap, for instance after resection. Thus, the second anatomical structure 22b can be configured as an implant, or the bone fixation system 20 can be configured to stabilize the first and second anatomical structures 22a and 22b relative to each other as described above, and further relative to a third anatomical structure, which can be bone or a bone implant. It should be appreciated, of course, that the bone fixation system 20 can be configured any number of anatomical structures relative to each other as desired. For instance, the fractured bone can be comminuted, and thus include any number of bone fragments that can be secured relative to each other by the bone fixation system 20. Otherwise stated, the bone fixation system 20 can be configured to be implanted onto bone so as to stabilize the bone with respect to one or more other anatomical structures. Alternatively or additionally, it will be appreciated that the links 30 can be attached to underlying bone, and adjusted relative to each other so as to reduce a bone gap defined between the bone fragments. Alternatively or additionally still, it will be appreciated that the links 30 can be attached to underlying bone, and adjusted relative to each other so as to manipulate the bone fragments.

The bone 24 is illustrated as a mandible in FIG. 1, though it should be appreciated that the bone can be defined by any suitable bone as desired in the human body, or other animal body, as desired, such as the pelvis, scapula, clavicle, wrist, spine, and the thorax region, including one or more ribs, the sternum, or the like. As is described in more detail below, the bone fixation linkage 26 is modular, adjacent ones of the interconnected links can angulate with respect to each other before they are locked to each other. In one example, the interconnected adjacent links can angulate in-plane relative to each other. In another example, the interconnected adjacent links can angulate out-of-plane relative to each other.

The term "in-plane" as used herein refers to a direction that is one or more up to all of 1) substantially parallel to an inner surface of the adjacent links that face the underlying anatomical structure, 2) substantially parallel to an outer surface of the adjacent links that is opposite the inner surface, 3) substantially normal to the central axis of one or more of fixation apertures that extend through one or both of the adjacent links, and 4) a direction whereby the central axis of at least one of the fixation apertures of a first one of the adjacent links and the central axis of at least one of the fixation apertures of a second one of the adjacent links has a relative orientation that is constant before and after in-plane articulation. In one example, the relative orientation can be substantially parallel. In another example, the relative orientation can be angularly offset. The term "substantially" as used herein takes into account manufacturing tolerances and movement that does not alter the nature of fixation to the underlying anatomical structure.

The term "out-of-plane" is used herein to refer to a direction that is one or more of 1) along a fixed or moving axis that is oriented substantially parallel to an inner surface of the adjacent links that face the underlying anatomical structure, 2) along a fixed or moving axis that is oriented substantially parallel to an outer surface of the adjacent links that is opposite the inner surface, 3) along a fixed or moving axis that is oriented substantially normal to one or more of fixation apertures that extend through one or both of the adjacent links, and 4) a direction whereby the central axis of at least one of the fixation apertures of a first one of the adjacent links and the central axis of at least one of the fixation apertures of a second one of the adjacent links defines a first relative orientation prior to out-of-plane articulation, and a second relative orientation different than the first relative orientation after out-of-plane articulation. In one example, the first relative orientation can be substantially parallel, and the second relative orientation can be angularly offset.

The bone fixation linkage 26 can be made from any suitable biocompatible material, including a metal such as titanium, stainless steel, or alloys thereof, or any suitable alternative implantable material, such as polymers based materials like poly-ether-ether-ketone (PEEK), or PEKK as desired. The material can also be a bio-resorbable material in certain examples.

Referring now to FIG. 2, the bone fixation linkage 26, and thus each of the links 30, can define an inner end 32a, which can define an inner surface, that is configured to face the underlying anatomical structure, such as the bone 24, and an outer end 32b that can define an outer surface opposite the inner end 32a. In one example, the inner end 32a of at least one or more up to all of the links 30 can be substantially planar. The inner end 32a can be said to be spaced from the outer end 32b in an inward direction. Similarly, the outer end 32b can be said to be spaced from the inner end 32a in an outward direction. Both the inward direction and the outward direction can be oriented along a transverse direction T. Directions within 45 degrees of the transverse direction T can be considered to be oriented along the transverse direction. At least a portion up to an entirety of the inner and outer surfaces can be elongate along a longitudinal direction L that is substantially perpendicular to the transverse direction T. Directions within 45 degrees of the longitudinal direction L can be considered to be oriented along the longitudinal direction. The linkage 26 can define a width along a lateral direction A that is substantially perpendicular to each of the transverse direction T and the longitudinal direction L. Directions within 45 degrees of the lateral direction A ca be considered to be oriented along the lateral direction. Each of the inner and outer ends 32a and 32b can be sized and shaped as desired, and can define any number of surfaces as desired, including at least one or more surfaces.

Each of the links 30 can include at least one first link 34 such as a plurality of first links 34, and at least one second link 36 such as a plurality of second links 36. The first and second links 34 and 36 can be alternatingly arranged with each other, and adjacent first and second links ones of the links 30 can be attached and locked to each other. When the adjacent ones of the first and second links 34 and 36 are attached to each other but unlocked from each other, the adjacent ones of the first and second links 34 and 36 can angulate with respect to each other. When the adjacent ones of the first and second links 34 and 36 are attached to each other and locked to each other, the adjacent ones of the first and second links 34 and 36 are prevented from angulating with respect to each other. As will be described in more detail below, one or more adjacent ones of the first and second links 34 and 36 can be configured to angulate in-plane to an in-plane angulated position with each other when unlocked from each other, and fixed in their in-plane angulated position when locked to each other. Alternatively or additionally, one or more adjacent ones of the first and second links 34 and 36 can be configured to angulate out-of-plane with each other to an out-of-plane angulated position when unlocked from each other, and fixed in their out-of-plane angulated position when locked to each other.

The combination of in-plane angulation and out-of-plane angulation allows the bone fixation linkage 26 to conform to the underlying anatomical structure. Further, the bone fixation linkage 26 can include any number of links 30 as desired depending on at least one of several factors, including on the desired length of the bone fixation linkage 26, the desired maneuverability of the bone fixation linkage 26, and the desired geometrical shape of the bone fixation linkage 26. In this regard, it should be appreciated that the links 30 can include any number of in-plane angulation connections between adjacent ones of the links 30 and out-of-plane angulation between adjacent ones of the links 30 as desired such that the bone fixation linkage 26 defines any size and shape so as to conform to the underlying anatomy of the underlying bone, which can be any suitable bone as desired, for instance one or more bones of the mandible, hand or the distal radius, among others. Further, it should be appreciated that the bone fixation linkage 26 can be configured to join two different types of bone plates. For instance, the bone fixation linkage 26 can connect to a hand bone plate at one end, and to a distal radius bone plate at another end.

Referring now to FIGS. 2-4A, at least one of the first links 34 can include a first in-plane attachment end 37 that includes a plurality of first locking ribs 38. At least one of the second links 36 can include a second in-plane attachment end 39 that includes a plurality of second locking ribs 40. At least one, such as a plurality of up to all, of the first and second in-plane attachment ends 37 and 39 of the locking ribs 38 and 40 are configured to mate with each other so as to lock the respective first and second links 34 and 36 to each other at a plurality of in-plane angulated relative positions between the first and second links 34 and 36. It should be appreciated that one of the first and second in-plane attachment ends 37 and 39 can include one locking rib, while the other of the first and second in-plane attachment ends 37 and 39 can have a plurality of ribs configured to receive the rib of the one of the first and second in-plane attachment ends 37 and 39 therebetween, so as to fix the in-plane position of the corresponding links. Thus, one of the first and second in-plane attachment ends 37 and 39 can include at least one rib, and the other of the first and second in-plane attachment ends 37 and 39 can include a plurality of ribs. In one example, both the first and second in-plane attachment ends 37 and 39 can include respective pluralities of ribs. The first and second locking ribs 38 and 40 can be referred to as first and second in-plane locking ribs. Thus, the at least one first locking rib 38 can mate with the at least one second locking rib 40 when the first and second links 34 and 36 are in a first in-plane position relative to each other. Further, the at least one first locking rib 38 can mate with the at least one second locking rib 40 when the first and second links 34 and 36 are in a second in-plane position relative to each other and different than the first in-plane position. It should be appreciated that the first and second links 34 and 36 are at the same out-of-plane position when the ribs 38 and 40 mate with each other in each of the first and second in-plane relative positions. For instance, one or both of the inner and outer surfaces of the first links 34 are in-plane with the respective one or both of the inner outer surfaces of the second links 36 when the first and second locking ribs 38 are mated with each other.

As will be appreciated from the description below, the at least one of the first locking ribs 38 is configured to mate with at least one of the second locking ribs 40 so as to lock the first link 34 to the adjacent second link 36 without expansion of either of the first and second links 34 and 36 relative to the other of the first and second links 34 and 36. For instance, it can be said that the second in-plane attachment end 39 of the second link 36 is unexpandable inside the first in-plane attachment end 37 of the first link 34 1) from a first position whereby the first ribs 38 are spaced from each other along a first path and the second ribs 40 are spaced from each other along a second path that is different than the first path such that the at least one first rib 38 is configured not to mate with the at least one second rib 40, 2) to a second expanded position whereby the first and second paths are substantially complementary to each other such that the at least one first rib 38 is configured to mate with the at least one second rib 40. Accordingly, as will be appreciated from the description below, the first and second locking ribs 38 and 40 are positioned such that the at least one of the first locking ribs 38 configured to mate with the at least one of the second locking ribs 40 so as to positionally lock the first link 34 to the adjacent second link 36 prior to insertion of a fixation member 50 into or through either of respective apertures 46 and 48 of the first and second links 34 and 36. Thus, the at least one of the first and second locking ribs 38 and 40 are sized and configured to mate with each other both when 1) the first and second locking ribs 38 and 40 are offset from each other along a direction perpendicular to the transverse direction T, and 2) the second in-plane attachment end 39 is configured to be received in the first in-plane attachment end 37.

When the at least one first rib 38 is mated with the at least one second rib 40, the first ribs 38 are spaced from each other along a plane and the second ribs 40 are spaced from each other along the plane, and the ribs 38 and 40 interfere with each other so as to prevent the first and second link 34 and 36 from rotating with respect to each other about an axis of rotation that is normal to the plane. For instance, the plane can be substantially parallel to the inner end. Further, the plane can be oriented substantially normal to the transverse direction T. Thus, the in-plane angulation can be along a plane that is oriented substantially normal to the transverse direction T. The axis of rotation can be oriented along the transverse direction T.

The first ribs 38 can include at least one group of first ribs that can be spaced from each other along an arcuate path. Similarly, the second ribs 40 of each group of second ribs 38 can be spaced from each other along a complementary arcuate path. For instance, the arcuate paths can be a substantially cylindrical path. In one example, all of the first ribs 38 are aligned with each other along the respective substantially cylindrical path. Similarly, all of the second ribs 40 can be aligned with each other along the respective substantially cylindrical path. One of the arcuate paths can be concave, while the other of the arcuate paths can be convex. In the illustrated example, the arcuate path defined by the first ribs 38 can be concave, and the arcuate path defined by the second ribs 40 can be convex. The substantially cylindrical paths can be defined by a substantially cylindrical shape having a central axis oriented along a direction that can be oriented substantially along the transverse direction T. The term "substantially cylindrical" as used herein recognizes that shapes and paths can deviate from a pure cylindrical shape without departing from the scope of the present disclosure.

The first in-plane attachment end 37 of the first link 34 can define a receptacle 42 and the second in-plane attachment end 39 of the second link 36 can define a plug 44 that is configured to be received by the receptacle 42. For instance, an inner surface of the first link 34 that at least partially defines the receptacle 42 can carry the first ribs 38. In one example, the first ribs 38 can be arranged in first and second groups of first ribs 38 that are disposed on opposite sides of the receptacle 42. For instance, the first and second groups of first ribs 38 can be disposed on opposite sides of the receptacle 42 along the lateral direction A. The second link 36 can define a main portion 45 and an arm 47 that extends from the main portion 45 and is monolithic with the main portion 45. The arm 47 can define the plug 44. The plug 44, and thus the arm 47, can carry the second ribs 40. The first ribs 38 can project inwardly from the inner surface. In particular, the first ribs 38 can project inwardly to distal tips. The distal tips of the first ribs 38 can be elongate along respective straight lines. The straight lines can be oriented parallel to each other. For instance, the distal tips can be elongate substantially along the transverse direction T. It should be appreciated, of course, that the distal tips can be alternatively shaped as desired. The second ribs 40 can project outwardly from the plug 44. In particular, the second ribs 40 can project inwardly to respective distal tips. The distal tips of the second ribs 40 can be elongate along respective straight lines. The straight lines can be oriented parallel to each other. For instance, the distal tips of the second ribs 40 can be elongate substantially along the transverse direction T. It should be appreciated, of course, that the distal tips can be alternatively shaped as desired.

The receptacle of the first link 34 can include an opening 49 that extends into the first link 34 along the longitudinal direction L, and has a width along the lateral direction A that is sized to receive the arm 47 of the second link 36. Further, the second ribs 40 can be arranged in first and second groups of second ribs 40 that extend out from opposite sides of the plug 44. For instance, the first and second groups of second ribs 40 that extend out from opposite sides of the plug 44 with respect to the lateral direction A. At least one of the first and second ribs 38 and 40 of the first groups are configured to mate with each other while at least one of the first and second ribs 38 and 40 of the second groups are mated with each other. It should be appreciated that the first ribs 38 can be arranged in any number of groups as desired, including at least one and a plurality of groups. The groups of first ribs 38 can be spaced from each other along any direction as desired, including one or both of the transverse direction T and the lateral direction A. Similarly, the first ribs 40 can be arranged in any number of groups as desired, including at least one and a plurality of groups. The groups of first ribs 40 can be spaced from each other along any direction as desired, including one or both of the transverse direction T and the lateral direction A.

The plug 44 is configured to be received in the receptacle 42 so as to cause the first and second ribs 38 and 40 to mate with each other. Thus, it can be said that the first link 34 receives the second link 36 when the first and second ribs 38 and 40 are mated to each other. During operation, the first and second links 36 can be oriented as desired relative to each other in-plane, and the ribs 38 and 40 can be aligned with each other along the transverse direction T. For instance, the second link 36 can be brought at least into proximity of, for instance against, the anatomical structure, and the first link 34 can subsequently be brought down onto the second link 36 in the inward direction such that the plug 44 is received in the receptacle 42 when the links 34 and 36 are in the desired second in-plane relative orientation, and the first and second ribs 38 and 40 to mate with each other.

The outer surface of the arm 47 can be recessed with respect to the outer surface of the main portion 45 along the transverse direction T. That is, the outer surface of the arm 47 can be offset with respect to the outer surface of the main portion 45 in the inward direction. Accordingly, then the plug 44 is disposed in the receptacle 42 and the ribs 38 and 40 are mated with each other, the outer surface of the main portion 45 can be substantially flush with the outer surface of the first link 34.

With continuing reference to FIGS. 2-4A, the first in-plane attachment end 37 of the first link 34 defines a respective first fixation aperture 46 that extends therethrough from the outer end 32b to the inner end 32a along a respective central axis. The central axis can be oriented along the transverse direction T. The first fixation aperture 46 can extend through the receptacle 42. Thus, the first and second groups of first ribs 38 can be disposed on opposite sides of the aperture 46. The first in-plane attachment end 37 of the first link 34 can define an outer ring 56. The outer ring 56 can be an enclosed outer ring. The outer ring 56 can define a portion of the outer surface of the first link 34. The outer ring 56 can at least partially define the first fixation aperture 46. The outer ring 56 can be offset from the ribs 38 along the outward direction. The first link 34 can further define a shelf 58 that is offset with respect to the outer ring 56 in the inward direction, and can extend into the first fixation aperture 46. The shelf 58 can carry the first ribs 38. For instance, the first ribs 38 can project inwardly from the shelf 58.

The second in-plane attachment end 39 of the second link 36 can define a respective first fixation aperture 48 that extends therethrough from the outer end 32b to the inner end 32a along a respective central axis. The central axis can be oriented along the transverse direction T. The first fixation aperture 48 can be spaced from the second ribs 40. For instance, the first and second groups of the second ribs 40 can be disposed on opposite sides of the first fixation aperture 48. The first fixation apertures 46 and 48 can be aligned with each other both when the first and second ribs 38 and 40 are aligned for mating along the transverse direction T, and when the first and second ribs 38 and 40 are mated with each other.

Referring also to FIGS. 4B-4C, the first fixation apertures 46 and 48 are configured to receive a first fixation member. The fixation member can be configured as the fixation member 50. The at least one of the first and second ribs 38 and 40 are configured to mate with each other prior to insertion of the first fixation member 50 through either of the first and second fixation apertures 46 and 48. The first fixation member 50 can be a bone fixation member 28. Thus, the first fixation member 50 includes a head 52 and a shaft 54 that extends from the head 52. The shaft 54 has a length sufficient so as to extend through the first fixation apertures 46 and 48 and into the underlying anatomical structure when the head 52 rests against the first link 34. In one example, the shaft 54 is threaded. It should be appreciated that the second link 36, and in particular the plug 44, can be captured between the underlying anatomical structure and the first link 34 when the first fixation member 50 is driven into the underlying anatomical structure. In one example, the head 52 of the first fixation member 50 can sit against the shelf 58 when fully inserted. Further, the first fixation member 50 can define a neck 60 that extends between the head 52 and the shaft 54. The neck 60 can be threaded. Similarly, the first fixation aperture 58 of the second link 36 can be threaded, such that the neck 60 can threadedly purchase with the second link 36 in the first fixation aperture 58. The shaft 54 can have a length sufficient to extend into the underlying anatomical structure as described above, such that the first fixation member 50 is a bone fixation member. Alternatively, the shaft 54 can be sufficiently short, or the first fixation member 50 can be devoid of a shaft 54, such that the first fixation member 50 can be configured to secure the first link to the second link without extending into the underlying anatomical structure. For instance, the shaft 54 can have a length that is extends from the head a distance less than the distance from the outer end 32b to the underlying bone along the transverse direction T. For instance, the length of the shaft 54 can be equal to or less than the distance from the inner end 32a to the outer end 32b along the transverse direction T.

As described above, the first ribs 38 can be arranged in at least one group of first ribs 38, such that the first ribs 38 of each group of first ribs 38 are spaced from each other along a respective arcuate path. Similarly, the second ribs 40 can be arranged in at last one group of second ribs 40, such that the second ribs of each group of second ribs 40 are spaced from each other along a respective complementary arcuate path. The arcuate path defined by the at least one group of first ribs 38 can be defined by a plane that is normal to the transverse direction T. In one example, all of the first ribs 38 of each group of first ribs 38 are spaced from each other along the plane that is normal to the transverse direction T, and aligned with each other along the plane that is normal to the transverse direction T. In another example, all of the first ribs 38 of each group of first ribs 38 can be spaced from each other and aligned with each other along a plane that is oriented substantially normal to the central axis of the first fixation aperture 46 of the first link 34. Similarly, the second ribs 40 of each group of second ribs 40 can be spaced from each other along a respective arcuate path. The respective arcuate path can be defined by a plane that is normal to the transverse direction T. In one example, all of the second ribs 40 of each group of second ribs 40 are spaced from each other along the plane that is normal to the transverse direction T, and aligned with each other along the plane that is normal to the transverse direction T. In another example, all of the second ribs 40 of each group of second ribs 40 can be spaced from each other and aligned with each other along a plane that is oriented normal to the central axis of the first fixation aperture 48 of the second link 36.

The second link 36 can define a second fixation aperture 62 that is spaced from the first fixation aperture 48 and extends from the outer surface of the second link 36 to the inner surface of the second link 36. The second fixation aperture 62 can extend through the second link along a central axis that is oriented along the transverse direction T. In one example, the second fixation aperture 62 extends through the main portion 45. The second fixation aperture 62 can be threaded so as to threadedly purchase with a fixation member, such as the bone fixation member 28. The second fixation aperture 62 is configured to receive a bone fixation member 28 that can include a head and a shaft that extends from the head. The head can be threaded. Alternatively, the bone fixation member 28 can include a neck that extends between the head and the shaft. The shaft can have a length sufficient to be driven into the underlying bone. Alternatively, the second fixation aperture 62 can be configured to receive a set screw having a shaft that extends from the head a distance less than the distance from the outer end 32b to the underlying bone along the transverse direction T. For instance, the shaft can have a length that is equal to or less than the distance from the inner end 32a to the outer end 32b along the transverse direction T. It should be appreciated that the second link 36 can include any number of second apertures 62 as desired. The second apertures 62 can be spaced from each other in any direction as desired. For instance, the second apertures can be spaced from each other along at least one or both of the longitudinal direction L and the lateral direction A. Thus, the second links 36 can be attached to the underlying bone at any one or more of a number of locations defined by the second apertures 62. The first link 34 can also define at least one up to a plurality of respective second fixation apertures spaced from the respective first fixation aperture 46 of the first link, the second fixation aperture of the first link 34 extending therethrough from the outer surface to the inner surface. As described above with respect to the second apertures 62, the second fixation apertures of the first link 34 can be spaced from each other along at least one or both of the longitudinal direction L and the lateral direction A, and can be configured to receive any suitable fixation member, such as a bone screw or a set screw.

A method for attaching the bone fixation linkage 26 to an underlying anatomical structure can include the step of placing the second link 36 against an underlying anatomical structure. The method can further include the step of bringing the first link 34 over the second link 36 so as to mate at least one of the first ribs 38 with at least one of second ribs 40 while the first link 34 is at one of a plurality of orientations relative to the second link 36, wherein at last one of the first ribs is configured to mate with at least one of the second ribs at each of the plurality of orientations. The orientations can be in-plane orientations. The method can further include the step of, inserting a bone fixation member through at least one of the first and second links 34 and 36 so as to attach the linkage to bone. The inserting step can be performed after the bringing step. The placing step can be performed before or after the bringing step. The method can further include the step of reducing at least first and second bone fragments, wherein the inserting step comprises attaching the linkage to each of the first and second bone fragments. The inserting step can include inserting the bone fixation member through at least one of the first and second links so as to attach the linkage to a first bone fragment of the bone. The method can further include the step of reducing a gap between the first bone fragment and a second bone fragment of the bone after the inserting step. After the reducing step, the method can include the step of inserting the bone fixation member through at least one of the first and second links so as to attach the linkage to the second bone fragment. The method can include the step of articulating the first and second links relative to each other so as to bring the first and second bone fragments toward each other. The articulating step can be performed before the ribs of the first and second links are mated with each other. Alternatively, mated ribs can be unmated to articulate the links relative to each other.

In-plane attachment ends of the first and second links 34 and 36 configured to lock to each other have been described above with respect to FIGS. 2-4C. Referring now to FIGS. 2 and 5-7B, at least one of the first links 34 can define a first out-of-plane attachment end 63, and at least one of the second links 36 can define a second out-of-plane attachment end 65 that are configured to lock to each other. The first out-of-plane attachment end 63 of the first link 34 can each include a plurality of first locking ribs 64. The second out-of-plane attachment end 65 of the second link 36 can each include a plurality of second locking ribs 66. At least one, such as a plurality of up to all, of the first and second locking ribs 64 and 66 are configured to mate with each other so as to lock the respective first and second links 34 and 36 to each other at a plurality of out-of-plane angulated relative positions between the first and second links 34 and 36. It should be appreciated that one of the first and second out-of-plane attachment ends 63 and 65 can include one locking rib, while the other of the first and second out-of-plane attachment ends 63 and 65 can have a plurality of ribs configured to receive the rib of the one of the first and second out-of-plane attachment ends 63 and 65 therebetween, so as to fix the in-plane position of the corresponding links. Thus, one of the first and second out-of-plane attachment ends 63 and 65 can include at least one rib, and the other of the first and second out-of-plane attachment ends 63 and 65 can include a plurality of ribs. In one example, both the first and second out-of-plane attachment ends 63 and 65 can include respective pluralities of ribs. The first ribs 64 can extend out to respective distal tips that can be elongate along respective straight lines. The straight lines can be oriented parallel to each other. For instance, the distal tips can be elongate substantially along the lateral direction A. It should be appreciated, of course, that the distal tips can be alternatively shaped as desired. The second ribs 66 can extend out to respective distal tips that elongate along respective straight lines. The straight lines can be oriented parallel to each other. For instance, the distal tips of the second ribs 66 can be elongate substantially along the lateral direction A. It should be appreciated, of course, that the distal tips can be alternatively shaped as desired.

The first and second locking ribs 64 and 66 can be referred to as first and second out-of-plane locking ribs. Thus, at least one first locking rib 64 of the first out-of-plane attachment end 63 can mate with at least one second locking rib 66 of the second out-of-plane attachment end 65 when the first and second links 34 and 36 are in a first out-of-plane position relative to each other. Further, the at least one first locking rib 64 can mate with the at least one second locking rib 66 when the first and second links 34 and 36 are in a second out-of-plane position relative to each other that is different than the first out-of-plane position. It should be appreciated that the first and second links 34 and 36 are at the same in-plane position when the ribs 64 and 66 mate with each other in each of the first and second out-of-plane relative positions. One or both of the inner and outer surfaces of the first links 34 are out-of-plane with the respective one or both of the inner outer surfaces of the second links 36 when the first and second locking ribs 64 and 66 in at least one of the first and second out-of-plane positions relative to each other.

As will be appreciated from the description below, the at least one of the first locking ribs 64 is configured to mate with at least one of the second locking ribs 66 so as to lock the first link 34 to the adjacent second link 36 without expansion of either of the first and second links 34 and 36 relative to the other of the first and second links 34 and 36. For instance, it can be said that the second out-of-plane attachment end 65 of the second link 36 is unexpandable inside the first in-plane attachment end 63 of the first link 34 1) from a first position whereby the first ribs 64 are spaced from each other along a first path and the second ribs 66 are spaced from each other along a second path that is different than the first path such that the at least one of the first ribs is configured not to mate with the at least one second rib 66, 2) to a second expanded position whereby the first and second paths are substantially complementary to each other such that the at least one first rib 64 mates with the at least one second rib 66. Accordingly, though in accordance with this example, the first at least one locking rib 64 in fact mates with the at least one second locking rib 66 upon insertion of a fixation member 50 through respective apertures 82 and 62 of the first and second links 34 and 36, the first and second locking ribs 64 and 66 are nevertheless positioned such the at least one of the first locking ribs 64 is configured to mate with at least one of the second locking ribs 66 so as to positionally lock the first link 34 to the adjacent second link 36 prior to insertion of the fixation member 50 into or through either of the apertures 82 and 62. Thus, the at least one of the first and second locking ribs 64 and 66 are sized to mate with each other both when 1) the first and second locking ribs 64 and 66 are offset from each other along a direction perpendicular to the transverse direction T, and 2) the second out-of-plane attachment end 65 is configured to be received in the first out-of-plane attachment end 63.

When the at least one first rib 64 is mated with the at least one second rib 66, the first ribs 64 are spaced from each other along a plane and the second ribs 66 are spaced from each other along the plane, and the ribs 64 and 66 interfere with each other so as to prevent the first and second link 34 and 36 from rotating with respect to each other about an axis of rotation that is normal to the plane. For instance, the plane can include the transverse direction T. Thus, the plane can be substantially orthogonal to the inner end of the first and second links 34 and 36. Thus, the out-of-plane angulation can be along a plane that is partially defined by the transverse direction T. The plane can be further defined by the longitudinal direction L defined as the direction of elongation of the first link 34, or at least a portion of the first link 34 that includes the out-of-plane attachment end. The axis of rotation for out-of-plane angulation can be oriented along a direction perpendicular to the transverse direction T. For instance, the axis of rotation for out-of-plane angulation can be oriented along the lateral direction A.

The first ribs 64 can be arranged in at least one group of first ribs 64 that are spaced from each other along an arcuate path. Similarly, the second ribs 66 can be arranged in at least one group of second ribs that are spaced from each other along a complementary arcuate path. One of the arcuate paths can be concave, while the other of the arcuate paths can be convex. For instance, the arcuate paths can be a substantially cylindrical path. In one example, all of the first ribs 64 are aligned with each other along the respective substantially cylindrical path. Similarly, all of the second ribs 66 can be aligned with each other along the respective substantially cylindrical path. In the illustrated example, the arcuate path defined by the first ribs 64 can be concave, and the arcuate path defined by the second ribs 66 can be convex. The substantially cylindrical paths can be defined by a cylinder having a central axis oriented along a direction angularly offset with respect to the transverse direction T. For instance, the direction can be oriented substantially along the lateral direction A.

The first out-of-plane attachment end 63 of the first link 34 can define a receptacle 68 and the second out-of-plane attachment end 65 of the second link 36 can define a plug 70 that is configured to be received by the receptacle 68. Thus, the plug 70 can extend in the receptacle 68 along a respective central axis that is oriented along the lateral direction A. In particular, the plug 70 of the second link 36 is configured to be received in the receptacle 68 of the first link 34 both when the first and second ribs 64 and 66 are mated with each other, and when the first and second ribs 64 and 66 are spaced from each other. For example, when the plug 70 is disposed in the receptacle 68, the first ribs 64 can be slidable with respect to the second ribs 66 between an unlocked position whereby the first and second ribs 64 and 66 are spaced from each other, and a locked position whereby at least one of the first ribs 64 is mated with at least one of the second ribs 66. The second link 36 can define a main portion 45 and an arm 72 that extends out from the main portion 45 and is monolithic with the main portion 45. The arm 72 can define a neck 74 and the plug 70 that extends from the neck 74. The plug 70, and thus the arm 72, can carry the second ribs 66. The outer surface of the neck 74 can be recessed with respect to the outer surface of the main portion 45.

The receptacle 68 of the first link 34 can include an opening 76 that extends into the first link 34 along the longitudinal direction L, and has a width along the lateral direction A that is sized to receive the neck 74 of the second link 36. When the outer surface of the neck 74 abuts the inner surface of the first link 34 in the receptacle 68, the outer surface of the main portion 45 can be substantially flush with the outer surface of the first link 34. Thus, the out-of-plane angulation in the outward direction can be limited to where the outer surface of the main portion 45 is substantially flush with the outer surface of the first link 34.

The first link 34 receives the second link 36 when the first and second ribs 38 and 40 are mated to each other. During operation, the first and second links 36 can be oriented as desired relative to each other out-of-plane, and the ribs 64 and 66 can be aligned with each other along the transverse direction T. For instance, the second link 36 can be brought into proximity, for instance against, the anatomical structure, and the first link 34 can subsequently be brought down onto the second link 36 in the inward direction such that the plug 70 is received in the receptacle 68 when the links 34 and 36 are in the desired second out-of-plane relative orientation. The first ribs 64 can be moved relative to the second ribs 66 to the locked position whereby at least one of the first ribs 64 mates with at least one of the second ribs 66. At least one bone fixation member 28 can attach one or both of the first and second links 34 and 36 to the underlying anatomical structure.

In one example, the first out-of-plane attachment end 63 of the first link 34 includes a latch 78 that is movable between a locked position whereby the first and second locking ribs 64 and 66 are mated with each other, and an unlocked position whereby the first and locking ribs 64 and 66 are spaced from each other. The latch 78 can be disposed in the receptacle 68. In particular, the first link 34 includes a first link body 80 that carries the latch 78. The latch 78 can carry the first ribs 64. The latch 78 is slidable with respect to the first link body 80 between the locked position and the unlocked position. For instance, the latch 78 can be slidable along the longitudinal direction with respect to the first link body 80 between the locked position and the unlocked position. The longitudinal direction L can be defined by a direction of elongation of the first link 34, or at least a portion of the first link 34 that defines the first out-of-plane attachment end 63. Further, in certain examples, the first link 34 can define a pair of apertures that extend from the first end 32a to the second end 32b and are spaced from each other along the longitudinal direction L. The first link body 80 can define the outer surface of the first link 34, and the latch 78 can be nested in the inner end of the first link 34. In one example, the inner end of the latch 78 does not protrude beyond the inner end of the first link body 80. The first and second links 34 and 66 can angulate out-of-plane with respect to each other at the respective first and second out-of-plane attachment ends 63 and 65 when the first ribs 64 are in the unlocked position. Thus, it can be said that the first and second links 34 and 66 can angulate out-of-plane with respect to each other at the respective first and second out-of-plane attachment ends 63 and 65 when the latch 78 is in the unlocked position.

The first out-of-plane attachment end 63 of the first link 34 can define a fixation aperture 82 that extends at least into the first link body 80 along a first aperture axis. The fixation aperture 82 can extend through the first link body 80 from the inner surface to the outer surface. The first aperture axis of the aperture 82 can be oriented along the transverse direction T. Further, the first fixation aperture 82 can be open to the latch 78 along a direction that is perpendicular to the aperture axis. For instance, the aperture 82 can be open to the latch 78 along the longitudinal direction L.

As described above, the first ribs 64 can include at least one group of first ribs 64 that are spaced from each other along a respective arcuate path, and the second ribs 66 can include at least one group of second ribs 66 that are spaced from each other along a respective complementary arcuate path. The arcuate path defined by the at least one group first ribs 64 can be defined by a plane that includes the transverse direction T. In one example, all of the first ribs 64 of each group of first ribs are spaced from each other along the respective plane that includes the transverse direction T, and aligned with each other along the plane that includes the transverse direction T. In another example, all of the first ribs 64 of each group of first ribs can be spaced from each other and aligned with each other along a respective plane that is substantially parallel to the central axis of the fixation aperture 82 of the first link 34. The plane can further include the central axis of the fixation aperture 82 of the first link 34. The plane of the arcuate path of the first ribs 64 can also include the longitudinal direction L. The at least one group of first ribs 64 can include one group or a plurality of groups that are spaced from each other in any direction as desired. For instance, the groups of first ribs 64 can be spaced from each other along one or both of the lateral direction A and the transverse direction T.

Similarly, the second ribs 66 of each group of second ribs 66 can be spaced from each other along a respective arcuate path. The respective arcuate path can be defined by a plane that includes the transverse direction T. In one example, all of the second ribs 66 of each group of second ribs 66 are spaced from each other along the plane that includes the transverse direction T, and aligned with each other along the plane that includes the transverse direction T. In another example, all of the second ribs 66 of each group of second ribs 66 can be spaced from each other and aligned with each other along a plane that is oriented parallel to the central axis of the fixation aperture 82. The plane of the arcuate path of the second ribs 66 can also include the longitudinal direction L. The at least one group of second ribs 64 can include one group or a plurality of groups that are spaced from each other, for instance along the lateral direction A.

The first out-of-plane attachment end 63 can be configured to receive a fixation member 50 in the fixation aperture 82. The shaft 54 of the fixation member 50 is configured to urge the latch 78 to move from the unlocked position to the locked position. In particular, when the shaft of the fixation member 50 is inserted into the fixation aperture 82 and moved to a position in alignment with the latch 78 along a direction perpendicular to the transverse direction T, the shaft 54 urges the latch 78 to move from the unlocked position to the locked position. Further, the shaft 54 can interfere with the latch 78 so as to prevent the latch 78 from moving from the locked position to the unlocked position. When the shaft 54 is removed from the fixation aperture 82, the latch 78 can be moved from the locked position to the unlocked position. When the fixation member 50 is inserted in the fixation aperture 82, the shaft 54 can terminate without extending into the underlying anatomical structure. Alternatively, the fixation member 50 can be configured as a bone fixation member 28 whereby the shaft 54 has a length sufficient to extend into the underlying anatomical structure. The fixation aperture 82 can be threaded, and the fixation member 50 can similarly be threaded so as to threadedly purchase with the first link 34 in the fixation aperture 82. For instance, the head 52 of the fixation member 50 can be threaded.

A method for attaching the bone fixation linkage 26 to an underlying anatomical structure can include the step of placing the second link 36 against an underlying anatomical structure. The method can further include the step of bringing the first link 34 over the second link 36 so as to mate at least one of the first ribs 38 with at least one of second ribs 40 while the first link 34 is at one of a plurality of orientations relative to the second link 36, wherein at last one of the first ribs is configured to mate with at least one of the second ribs at each of the plurality of orientations. The orientations can be out-of-plane orientations. The method can further include the step of inserting a bone fixation member through at least one of the first and second links 34 and 36 so as to attach the linkage to bone. The inserting step can be performed after the bringing step. The placing step can be performed before or after the bringing step. The method can further include the step of reducing at least first and second bone fragments, wherein the inserting step comprises attaching the linkage to each of the first and second bone fragments. The inserting step can include inserting the bone fixation member through at least one of the first and second links so as to attach the linkage to a first bone fragment of the bone. The method can further include the step of reducing a gap between the first bone fragment and a second bone fragment of the bone after the inserting step. After the reducing step, the method can include the step of inserting the bone fixation member through at least one of the first and second links so as to attach the linkage to the second bone fragment. The method can include the step of articulating the first and second links relative to each other so as to bring the first and second bone fragments toward each other. The articulating step can be performed before the ribs of the first and second links are mated with each other. Alternatively, mated ribs can be unmated to articulate the links relative to each other.

Figure 9A:
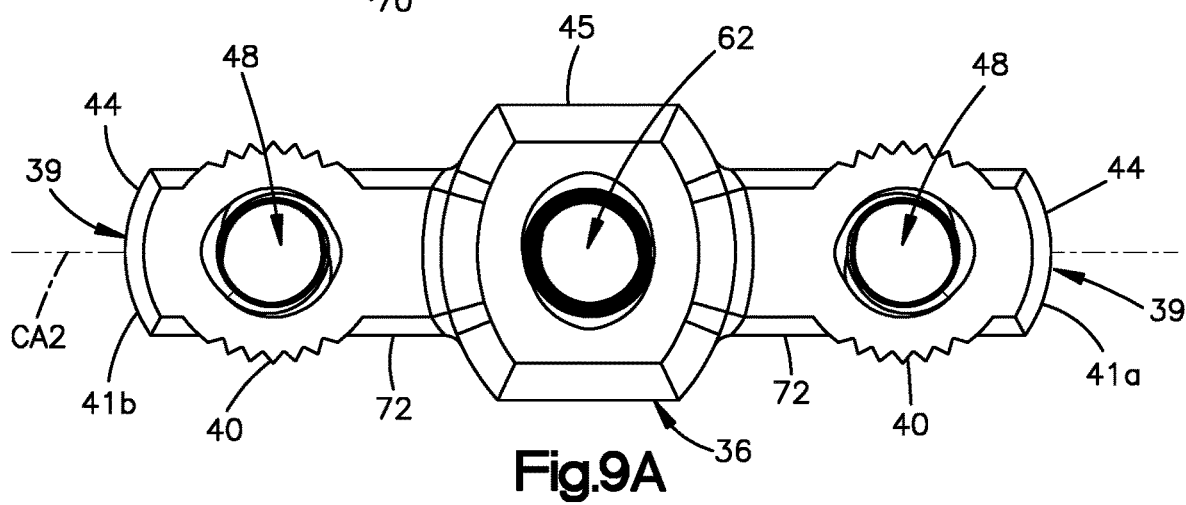
FIG. 9A is a perspective view of one of the second links of the linkage illustrated in FIG. 2, shown having first and second attachment ends in accordance with an alternative embodiment.
Figure 9B:
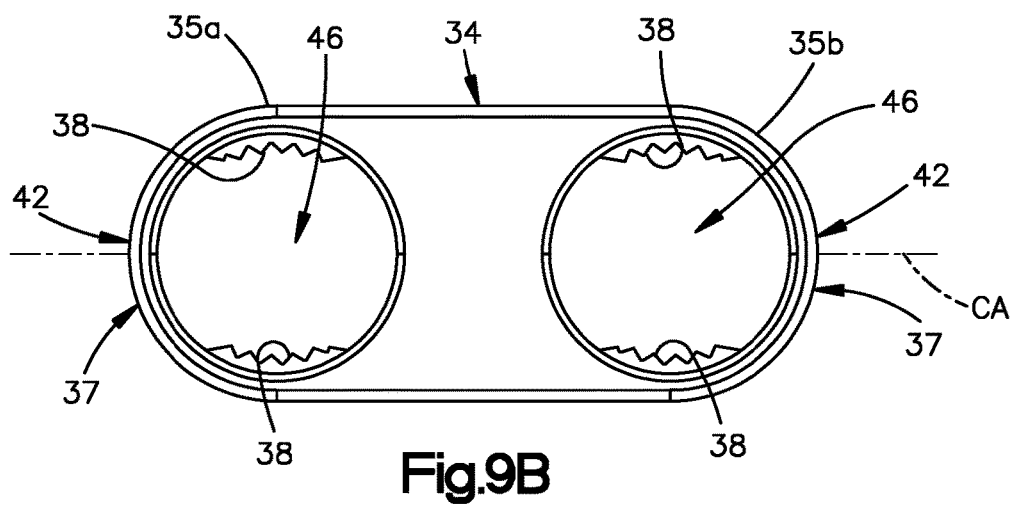
FIG. 9B is a perspective view of one of the first links of the linkage illustrated in FIG. 2, shown having first and second attachment ends in accordance with an alternative embodiment.

Referring now to FIGS. 3 and 9B, the first links 34 can each define a first end 35a and a second end 35b opposite the first end 35a along a central axis of elongation CA of the first link. At least one or both of the first and second ends 35a and 35b of at least one or more of the first links 34 up to all of the first links 34 can include at least one of the in-plane attachment end 37 and at least one of the out-of-plane attachment end 63 as described above. For instance, as illustrated in FIG. 9B, each of the first and second ends 35a and 35b of at least one or more of the first links 34 up to all of the first links 34 can include the in-plane attachment end 37. Alternatively, as illustrated in FIG. 3, one of the first and second ends 35a and 35b can include the in-plane attachment end 37, and the other of the first end second ends 35a and 35b of at least one or more of the first links 34 up to all of the first links 34 can include the out-of-plane attachment end 63. Thus, it can be said that at least one or both of the first and second ends 35a and 35b of at least one or more of the first links 34 up to all of the first links 34 can include at least one of the in-plane attachment end 37. Alternatively still, if desired, each of the first and second ends 35a and 35b of at least one or more of the first links 34 up to all of the first links 34 can include the out-of-plane attachment end 63. Thus, it can be said that at least one or both of the first and second ends 35a and 35b of at least one or more of the first links 34 up to all of the first links 34 can include the out-of-plane attachment end 63.

Similarly, referring now to FIGS. 3, 5, 8, and 9A, the second links 36 can each define a first end 41a and a second end 41b opposite the first end 35a along a central axis of elongation CA2 of the second link. The central axis CA2 can extend through each of the first and second ends 41a and 41b. For instance, the central axis CA2 can extend centrally through each of the first and second ends 41a and 41b with respect to the lateral direction A. In one embodiment the second links 36 can include at least one terminal end link, such as a pair of terminal links at opposed ends of the linkage 26. It should be appreciated that the bone fixation linkage 26 can terminate at a pair of outermost terminal links. One or both of the terminal links of the bone fixation linkage 26 can be defined by the second link 36. Alternatively or additionally, one or both of the terminal links of the bone fixation linkage 26 can be defined by the first link 34.

Figure 8:
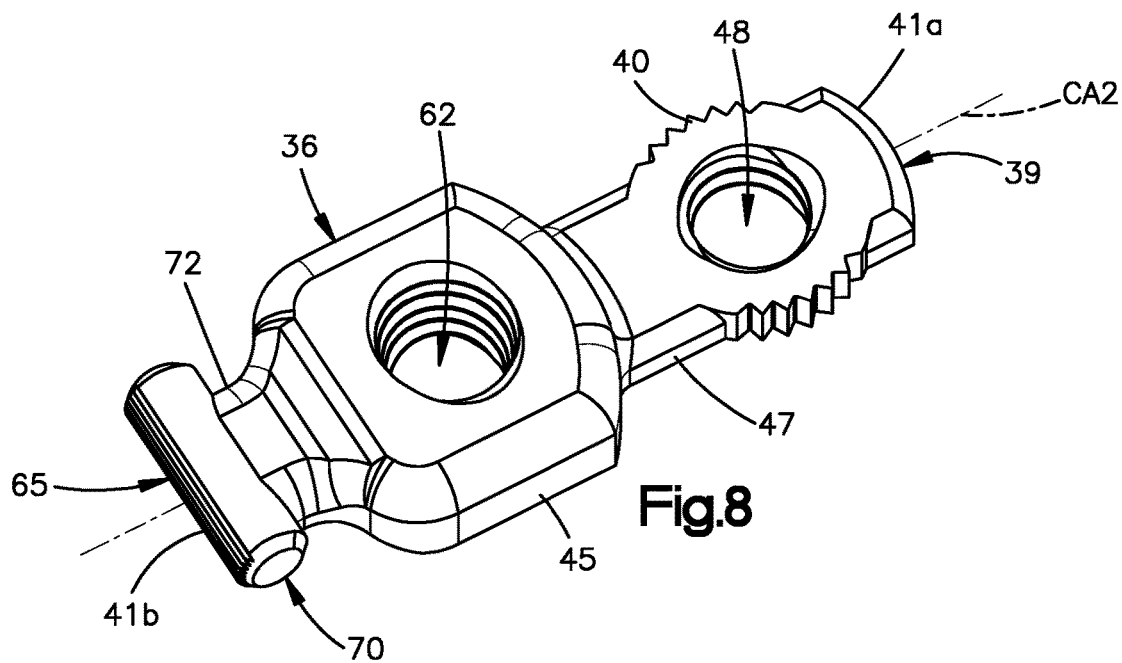
FIG. 8 is a perspective view of one of the second links of the linkage illustrated in FIG. 2, shown having first and second attachment ends in accordance with one embodiment.

One of the first and second ends 41a and 41b of each terminal links can include the main body portion 45, and the other of the first and second ends 41a and 41b can include one of the in-plane attachment end 39 and the out-of-plane attachment end 65. For instance, one of the first and second ends 41a and 41b can define the main body portion 45, and the other of the first and second ends 41*a* and 41*b* can define the in-plane attachment end 39 as illustrated in FIG. 3. Alternatively, one of the first and second ends 41*a* and 41*b* can define the main body portion 45, and the other of the first and second ends 41*a* and 41*b* can define the out-of-plane attachment end 65 as illustrated in FIG. 5. Alternatively still, as illustrated in FIGS. 8 and 9A, at least one or both of the first and second ends 41*a* and 41*b* of at least one or more of the second links 36 up to all of the second links 36 can include at least one of the in-plane attachment end 39 and at least one of the out-of-plane attachment end 65 as described above. For instance, as shown in FIG. 8, one of the first and second ends 41*a* and 41*b* can include the in-plane attachment end 39, and the other of the first and second ends 41*a* and 41*b* can include the out-of-plane attachment end 65. Alternatively, as illustrated in FIG. 9A, the first end 41*a* can include the in-plane attachment end 39, and the second end 41*b* can include the in-plane attachment end 39. Alternatively still, each of the first and second ends 41*a* and 41*b* can include the out-of-plane attachment end 65 as desired.

It is further appreciated that the first and second links 34 and 36 can define any suitable geometry as desired. For instance, as illustrated in FIG. 3, the central axis CA of at least one or more up to all of the first links 34 can define a straight line from the first end 35*a* to the second end 35*b*. The straight line can be oriented along the longitudinal direction L. The central axis CA can extend each of the first and second ends 35*a* and 35*b*. For instance, the central axis CA can extend centrally through each of the first and second ends 35*a* and 35*b* with respect to the lateral direction A. In another example illustrated in FIG. 1, the central axis CA of at least one of the first links 34' can define a first portion and a second portion that is angularly offset in-plane with respect to the first portion. Thus, the first link 34' can define a first portion and a second portion elongated along directions angularly offset in-plane relative to each other. In one example, the central axis CA can define an in-plane elbow at an interface of the first and second portions of the central axis CA. At least one or both of first and second portions of the central axis CA can be linear. Alternatively or additionally, at least one or both of first and second portions of the central axis CA can be nonlinear or curved.

Alternatively, referring to FIG. 10, the central axis CA of at least one of the first links 34 can define a first portion and a second portion that is angularly offset with respect to the first portion out-of-plane. Thus, the first link 34 can define a first portion and a second portion elongated along directions angularly offset out-of-plane with respect to each other. In one example, the central axis CA can define an out-of-plane elbow at an interface of the first and second portions of the central axis CA. At least one or both of first and second portions of the central axis CA can be linear. Alternatively or additionally, at least one or both of first and second portions of the central axis CA can be nonlinear curved. Alternatively still, the central axis CA of at least one of the links 34 can define a first portion and a second portion that is angularly offset with respect to the first portion both out-of-plane and in-plane. Thus, the first link 34 can define a first portion and a second portion elongated along directions angularly offset both in-plane and out-of-plane with respect to each other. Accordingly, the elbow can be both an in-plane elbow and an out-of-plane elbow.

It should be appreciated that the bone fixation linkage 26 has been described above in accordance with one example, and that other examples of bone fixation linkage 26 are contemplated the offer the desired relative motion characteristic of the links. For instance, referring now to FIGS. 11-13C, the bone fixation linkage 26 includes a plurality of links 130 that are configured to be interconnected to each other. Each of the links 130 can define a first end 135*a* and a second end 135*b* opposite the first end 135*a*. The first ends 135*a* can each include a first out-of-plane attachment end 163, and the second ends 135*b* can each include a second out-of-plane attachment end 165. The first out-of-plane attachment ends 163 of each at least one or more up to all of the links 130 are configured to attach to the second out-of-plane attachment ends 165 of at least one or more up to all others of the links 130. In particular, the first out-of-plane attachment ends 163 are configured to attach to the second-out-of-plane attachment ends 165 at one of a plurality of out-of-plane positions, and at a fixed in-plane position.

The first out-of-plane attachment end 163 can include a plurality of first locking ribs 164. The second out-of-plane attachment end 165 can each include a plurality of second locking ribs 166. At least one of the first locking ribs 164 is configured to mate with at least one of the second locking ribs 166 so as to lock respective first and second adjacent ones of the links 130 to each other at a plurality of out-of-plane angulated relative positions between the first and second ones of the links 130. The first and second ones of the links 130 can be alternatingly arranged along the length of the bone fixation linkage. The first and second locking ribs 164 and 166 can be referred to as first and second out-of-plane locking ribs. Thus, at least one first locking rib 164 of the first out-of-plane attachment end 163 can mate with at least one second locking rib 166 of the second out-of-plane attachment end 165 when the first and second ones of the links 130 are in a first out-of-plane position relative to each other. Further, the at least one first locking rib 164 can mate with the at least one second locking rib 166 when the first and second ones of the links 130 are in a second out-of-plane position relative to each other that is different than the first out-of-plane position. It should be appreciated that the first and second ones of the links 130 are at the same in-plane position when the ribs 164 and 166 mate with each other in each of the first and second out-of-plane relative positions. One or both of the inner and outer surfaces of the first one of the links 130 can be out-of-plane with the respective adjacent second one of the links 130 when the first and second locking ribs 164 and 166 in at least one of the first and second out-of-plane positions relative to each other.

As will be appreciated from the description below, the at least one of the first locking ribs 164 is configured to mate with at least one of the second locking ribs 166 so as to lock the first one of the links 130 to the adjacent second one of the links 130 without expansion of either of the first and second ones of the links 130 relative to the other of the first and second ones of the links 10. For instance, it can be said that the second out-of-plane attachment end 165 is unexpandable inside the first in-plane attachment end 163 1) from a first position whereby the first ribs 164 are spaced from each other along a first path and the second ribs 166 are spaced from each other along a second path that is different than the first path such that the at least one of the first ribs 164 is configured not to mate with the at least one second rib 166, 2) to a second expanded position whereby the first and second paths are substantially complementary to each other such that the at least one first rib 164 is configured to mate with the at least one second rib 166. Accordingly, the first and second locking ribs 164 and 166 are positioned such the at least one of the first locking ribs 164 is configured to mate with at least one of the second locking ribs 166 so as to positionally lock the first one of the links 130 to the adjacent second one of the links 10 prior to insertion of the fixation member 50 into or through either of the apertures 182 and 184. Thus, the at least one of the first and second locking ribs 164 and 166 are sized to mate with each other both when 1) the first and second locking ribs 164 and 166 are offset from each other along a direction perpendicular to the transverse direction T, and 2) the second out-of-plane attachment end 165 is configured to be received in the first out-of-plane attachment end 163.

When the at least one first rib 164 is mated with the at least one second rib 166, the first ribs 164 are spaced from each other along a plane and the second ribs 166 are spaced from each other along the plane. The ribs 164 and 166 interfere with each other so as to prevent the first and second ones of the links 130 from rotating with respect to each other about an axis of rotation that is normal to the plane. For instance, the plane can include the transverse direction T. Thus, the plane can be substantially orthogonal to the inner end of the first and second ones of the links 130. Thus, the out-of-plane angulation can be along a plane that is partially defined by the transverse direction T. The plane can be further defined by the longitudinal direction L defined as the direction of elongation of the first one of the links 130, or at least a portion of the first one of the links 130 that includes the out-of-plane attachment end. The axis of rotation for out-of-plane angulation can be oriented along a direction perpendicular to the transverse direction T. For instance, the axis of rotation for out-of-plane angulation can be oriented along the lateral direction A.

The first ones of the ribs 164 can be spaced from each other along an arcuate path. Similarly, the second ones of the ribs 166 can be spaced from each other along a complementary arcuate path. One of the arcuate paths can be concave, while the other of the arcuate paths can be convex. The concave arcuate path can be concave with respect to the inner end 22a, while the convex arcuate path can be convex with respect to the outer end 22b. For instance, the arcuate paths can be a substantially cylindrical path. In one example, all of the first ribs 164 are aligned with each other along the respective substantially cylindrical path. Similarly, all of the second ribs 166 can be aligned with each other along the respective substantially cylindrical path. The substantially cylindrical paths can be defined by a cylinder having a central axis oriented along a direction angularly offset with respect to the transverse direction T. For instance, the direction can be oriented substantially along the lateral direction A. In the illustrated example, the arcuate path defined by the first ribs 164 can be concave, and the arcuate path defined by the second ribs 166 can be convex. Thus, the first out-of-plane attachment ends 163 can define plugs 170, and the second out-of-plane attachment ends 165 can define receptacles 168 sized and shaped to receive the plugs 170 of the first out-of-plane attachment ends 163. The plugs 170 can carry the first ribs 164, and the receptacles 168 can carry the second ribs 166.

In particular, the first ribs 164 can project out from the plugs 170 to respective distal tips. The first ribs 164 can extend outwardly. The distal tips of the first ribs 164 can be elongate along respective straight lines. The straight lines can be oriented parallel to each other. For instance, the distal tips of the first ribs 164 can be elongate substantially along the lateral direction A. It should be appreciated, of course, that the distal tips can be alternatively shaped as desired. The second ribs 166 can project out from at least one inner surface that defines the receptacle 168. Thus, the second ribs 166 can project inwardly. In particular, the second ribs 166 can project inwardly to respective distal tips. The distal tips of the second ribs 166 can be elongate along respective straight lines. The straight lines can be oriented parallel to each other. For instance, the distal tips of the second ribs 166 can be elongate substantially along the lateral direction A. It should be appreciated, of course, that the distal tips can be alternatively shaped as desired.

With continuing reference to FIGS. 11-13B, the outer surface of the first out-of-plane attachment end 163 can be recessed with respect to the outer end of the second out-of-plane attachment end in the inward direction. Accordingly, the linkage can maintain a low profile when the at least one inner surface of the second one of the links 130 that defines the receptacle 168 rests on the plug 170 of the first one of the links 130 so as to cause the respective at least one of the ribs 164 and 166 to mate with each other. In one example, the first and second ones of the plurality of links 130 can be identical to each other. Alternatively or additionally, as will be described in more detail below, at least one of the links 130 can geometrically differ from at least one other of the links 130.

The links 130 can define a link body 180, and the first out-of-plane attachment end 163 can define a first fixation aperture 182 that extends at least into the first link body 80 along a first aperture axis. The first aperture axis can be oriented along the transverse direction T. In one example, the he fixation aperture 182 can extend through the first link body 80 from the inner surface to the outer surface. The links 130 can further define a second fixation aperture 184 that extends through the second out-of-plane attachment end 163 from the outer surface to the inner surface. The first fixation aperture 182 of the first one of the links 130 is configured to align with the second fixation aperture 184 of the second one of the links 130 when the ribs 164 and 166 are mated with each other.

As described above, the first ribs 164 can be spaced from each other along a respective arcuate path, and the second ribs 166 can be spaced from each other along a respective complementary arcuate path. The arcuate path defined by the first ribs 164 can be defined by a plane that includes the transverse direction T. In one example, the first ribs 164 can include at least one group of first ribs 164 that are spaced from each other along a respective plane that includes the transverse direction T, and aligned with each other along the plane that includes the transverse direction T. In another example, all of the first ribs 164 of each group of first ribs 164 can be spaced from each other and aligned with each other along a respective plane that is parallel to the central axis of the fixation aperture 82 of the first link 34. The plane of the arcuate path of the first ribs 164 can also include the longitudinal direction L. Similarly, the second ribs 166 of each group of second ribs 166 can be spaced from each other along a respective arcuate path. The respective arcuate path can be defined by a plane that includes the transverse direction T. In one example, all of the second ribs 166 of each group of second ribs 166 are spaced from each other along the respective plane that includes the transverse direction T, and aligned with each other along the plane that includes the transverse direction T. In another example, all of the second ribs 166 of the group of second ribs 166 can be spaced from each other and aligned with each other along a plane that is oriented parallel to the central axis of the second fixation aperture 184. The plane of the arcuate path of the second ribs 66 can also include the longitudinal direction L.

The first fixation aperture 182 can be is encircled by the link body 180 at the first out-of-plane attachment end 163 along a plane that passes through the first fixation aperture 182 and is normal to the central axis of the first fixation aperture 182. For instance, the first fixation aperture 182 can have a circular cross-section. It should be appreciated, of course, that the first fixation aperture 182 can define any suitably shaped cross-section as desired. In one example, the first ribs 164 can be arranged in first and second groups of first ribs 164 that are disposed on opposite sides of the first fixation aperture 182. For instance, the first and second groups of first ribs 164 can be disposed on opposite sides of the receptacle 42 along the lateral direction A. The ribs 164 of the first group of first ribs 164 can be aligned with respective ones of the ribs 164 of the second group of first ribs 164.

The second fixation aperture 184 can be open to an external perimeter of the second one of the links 130 along a plane that passes through the second fixation aperture 184 and is oriented substantially normal to the central axis of the second aperture 184. For instance, the second fixation aperture can be open to the external perimeter of the second one of the links 130 along the longitudinal direction L. Thus, the second out-of-plane attachment end 165 can be forked. In particular, the second out-of-plane attachment end 165 can define first and second tines 167 that project out from the link body 180 along the longitudinal direction L and are spaced from each other along the lateral direction A. The second fixation aperture 184 can be defined between the tines 167. Alternatively, the second fixation aperture 184 can be enclosed by the link body 180 along the plane that passes through the second fixation aperture 184 and is oriented substantially normal to the central axis of the second aperture 184. In particular, the second fixation aperture 184 can be oval shaped having its major axis oriented along the longitudinal direction L. Accordingly, the second out-of-plane attachment end 165 can have clearance with respect to a received fixation member as the second one of the links 130 is disposed at one of a range of different out-of-plane positions relative to the first one of the links 130.

The first and second ones of the links 134 136 are configured to receive a fixation member 50 that extends through the second fixation aperture 184 and at least into the first fixation aperture 182 in the inward direction. In particular, the fixation member 50 can be configured to secure the first and second links together, for instance at the first out-of-plane attachment end 163 and the second out-of-plane attachment end 165, respectively, such that the at least one of the first ribs 164 is mated with the at least one of the second ribs 166. In one example, the head 52 can bear against the outer surface of the second one of the links 130. In particular, the head 52 can bear against the tines 167, and the shaft 54 can purchase in the underlying anatomical structure, thereby capturing the second one of the links 130 between the head 52 and the first one of the links 130, and capturing the first one of the links 130 between the underlying anatomical structure and the second one of the links 130. Alternatively, the first fixation aperture 182 can be threaded. The fixation member 50 can also be threaded and configured to purchase with the first one of the links 130 in the first fixation aperture 182. Accordingly, the second one of the links 130 can be captured between the head 52 and the first one of the links 130. In one example, the fixation member can have a threaded neck 60 disposed between the head 52 and the shaft 54. The threaded neck 60 can be configured to threadedly mate with the first one of the links 130 in the first fixation aperture 182. Alternatively or additionally, the shaft 54 can be threaded, and can have a length sufficient to purchase in the underlying anatomical structure. Thus, the fixation member 50 can be configured to secure the first and second ones of the links 130 to each other, and can be further configured as a bone fixation member 28.

A method for fixing the bone fixation system including the linkage 20 having the links 130 to an underlying anatomical structure is also contemplated. The method can include the step of mating the at least one of the second ribs 166 with the at least one of the first ribs 164, and driving the fixation member 50 through each of the first and second ones of the links 130 so as to secure the at least one second rib 166 to the at least one first rib 164. For instance, the driving step can include threadly mating the fixation member 50 to the first one of the links 130. The method can include the step of placing the first one of the links 130 against an anatomical structure before the mating step. The mating step can include the step of placing the second one of the links against the anatomical structure after the first one of the links 130 has been placed against the anatomical structure. The method can include the step of placing the first one of the links 130 against the anatomical structure after the mating step. The step of placing the first one of the links 130 against the anatomical structure can include the step of placing the second one of the links 130 against the anatomical structure. The method can include the step of attaching first and second ones of the links 130 to respective first and second bone fragments. The method can further include the step of reducing a gap between the first and second bone fragments before or after the attaching step. The reducing step can include the step of changing a relative orientation of the first and second links, and mating the first and second ribs. For instance, the mated ribs can be unmated prior to changing the relative orientation of respective ones of the links of the linkage.

As described above, each of the links 130 can define a first end 135a and a second end 135b opposite the first end 135a along a central axis of elongation CA of the first link. As described above, the first end 135a can include the first out-of-plane attachment member 163, and the second end 135b can include the second out-of-plane attachment member. Alternatively, both the first and second ends 135a and 135b at least a first one of the links 130 including a first plurality of the links 130 can include the first out-of-plane attachment end 163. Conversely, both the first and second ends 135a and 135b at least a second one of the links 130 including a second plurality of the links 130 can include the second out-of-plane attachment end 165. The first out-of-plane attachment ends 163 of the at least first one of the links 130 can attach to the second out-of-plane attachment ends 165 of an adjacent second one of the links 130. Further, one or both of the first and second ones of the links 130 can define at least one link having a terminal end that is not configured to attach to an adjacent one of the links 130. The links 130 having the terminal end can define opposed terminal ends of the bone fixation linkage.

Figure 12:
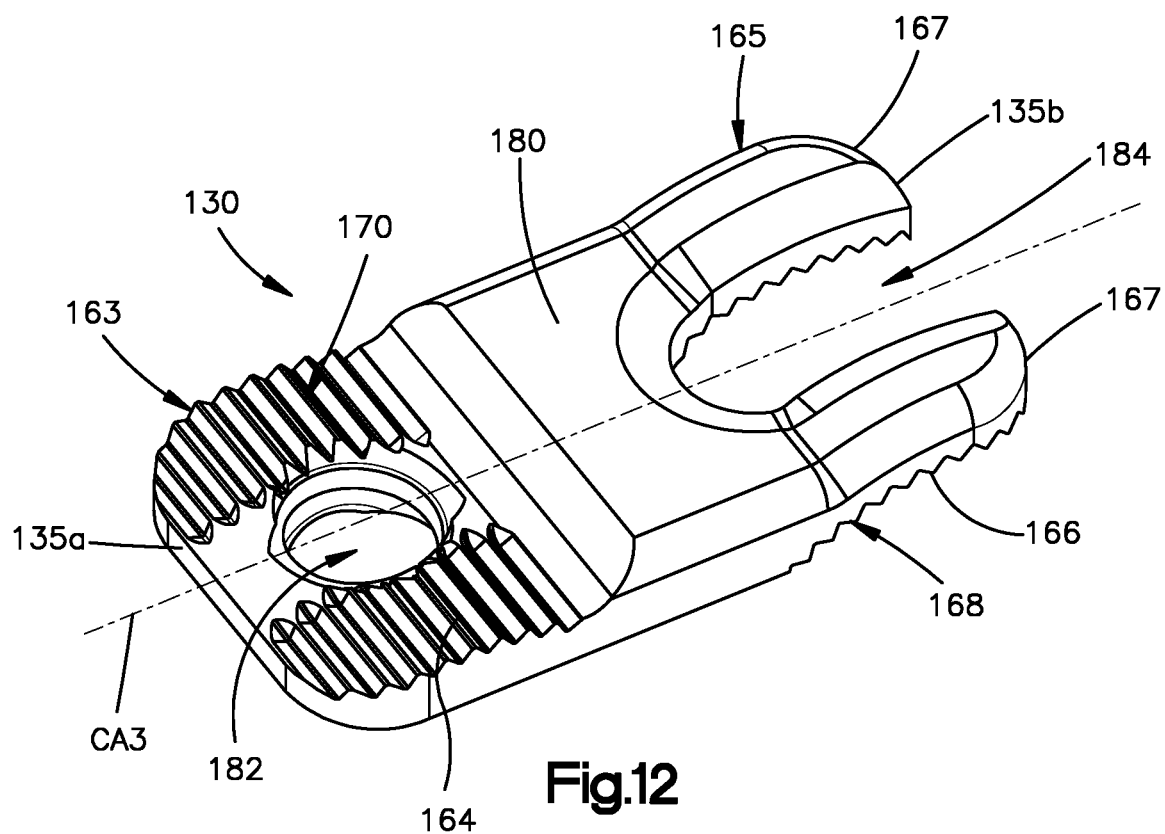
FIG. 12 is a perspective view of a bone fixation link of the bone fixation linkage illustrated in FIG. 11.
Figure 13A:
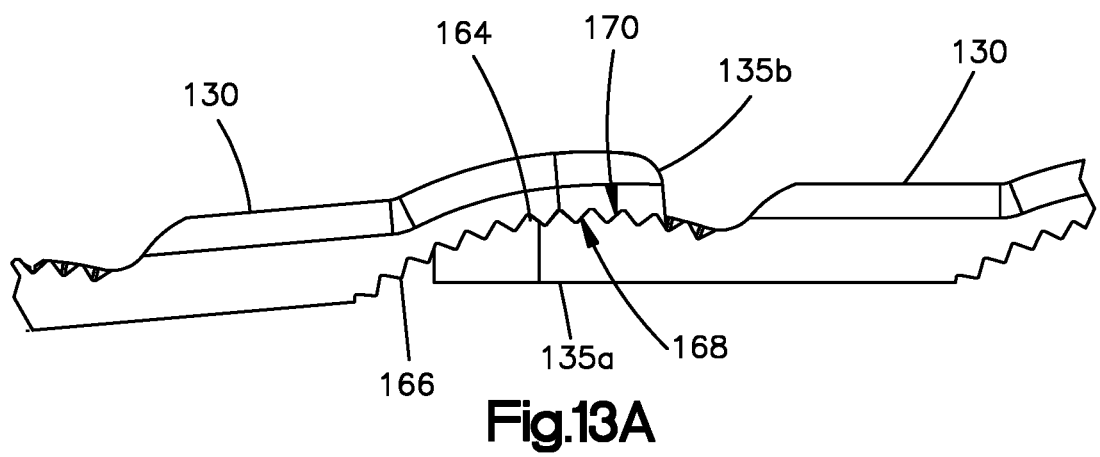
FIG. 13A is a side elevation view of first and second ones of the bone fixation links illustrated in FIG. 12 shown attached to each other.
Figure 14A:
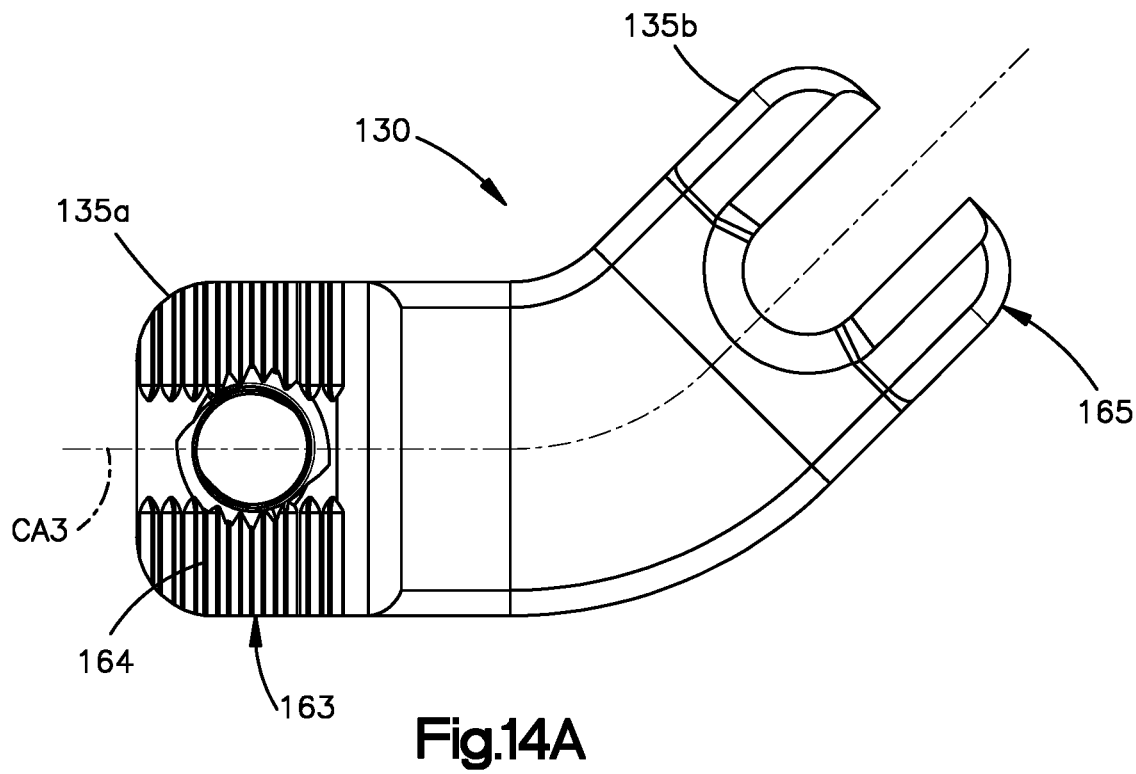
FIG. 14A is a top plan view of one of the first links of the linkage illustrated in FIG. 11, shown having an in-plane elbow in accordance with an alternative embodiment.

Further, as shown in FIG. 12, the first and second ends 135a and 135b of at least one of the links 130 up to all of the links can be opposite each other along the longitudinal direction L. Thus, the links 130 can be elongate along a central axis CA3 that is oriented along the longitudinal direction L and extends through each of the first and second ends 135a and 135b. For instance, the central axis CA3 can extend centrally through each of the first and second ends 135a and 135b with respect to the lateral direction A. The central axis CA3 can extend along a straight linear path from the first end 135a to the second end 135b. In another example, as illustrated in FIG. 14A, the central axis CA3 of at least one of the links 130 can define a first portion and a second portion that is angularly offset in-plane with respect to the first portion. Thus, the at least one of the links 130 can define a first portion and a second portion elongated along directions angularly offset in-plane relative to each other. In one example, the central axis CA3 can define an in-plane elbow at an interface of the first and second portions of the central axis CA3. At least one or both of first and second portions of the central axis CA3 can be linear. Alternatively or additionally, at least one or both of first and second portions of the central axis CA can be nonlinear or curved. It should be appreciated, of course, that the at least one of the links 130 can define any suitable pre-formed shape as desired between the first and second ends 135a and 135b.

Figure 14B:
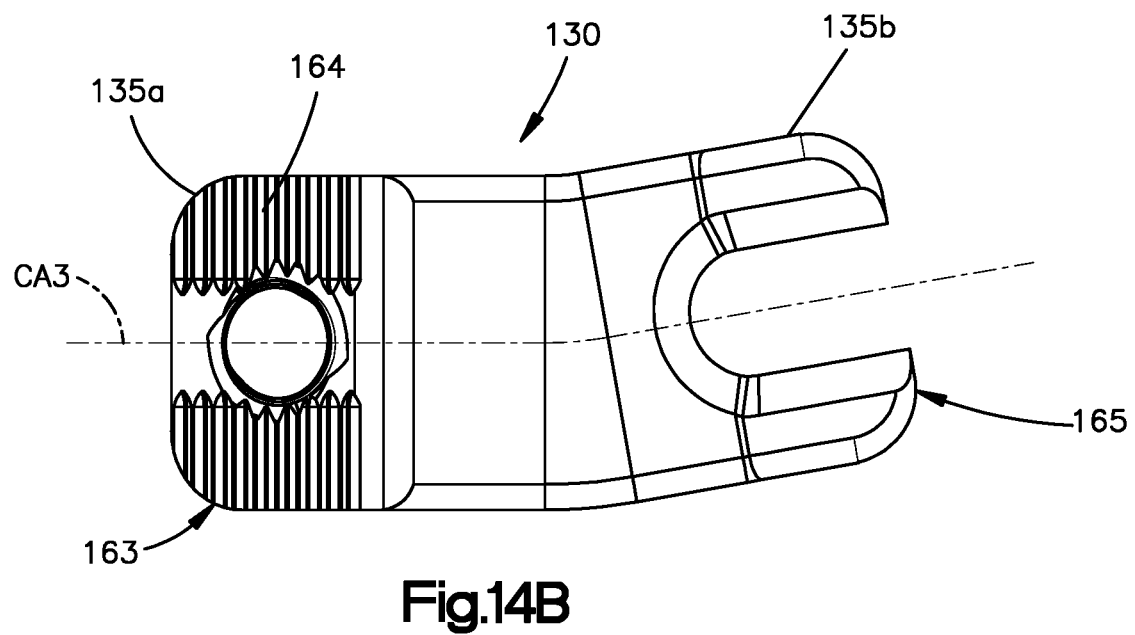
FIG. 14B is a top plan view of one of the first links of the linkage illustrated in FIG. 11, shown having an out-of-plane elbow in accordance with an alternative embodiment.

Alternatively, referring to FIG. 14B, the central axis CA3 of at least one of the links 34 can define a first portion and a second portion that is angularly offset with respect to the first portion out-of-plane. Thus, at least one of the links 130 can define a first portion and a second portion elongated along directions angularly offset out-of-plane with respect to each other. In one example, the central axis CA3 can define an out-of-plane elbow at an interface of the first and second portions of the central axis CA3. At least one or both of first and second portions of the central axis CA3 can be linear. Alternatively or additionally, at least one or both of first and second portions of the central axis CA3 can be nonlinear. Alternatively still, the central axis CA3 of at least one of the links 130 can define a first portion and a second portion that is angularly offset with respect to the first portion both out-of-plane and in-plane. Thus, the at least one of the links 130 can define a first portion and a second portion elongated along directions angularly offset both in-plane and out-of-plane with respect to each other. Accordingly, the elbow can be both an in-plane elbow and an out-of-plane elbow.

Figure 14C:
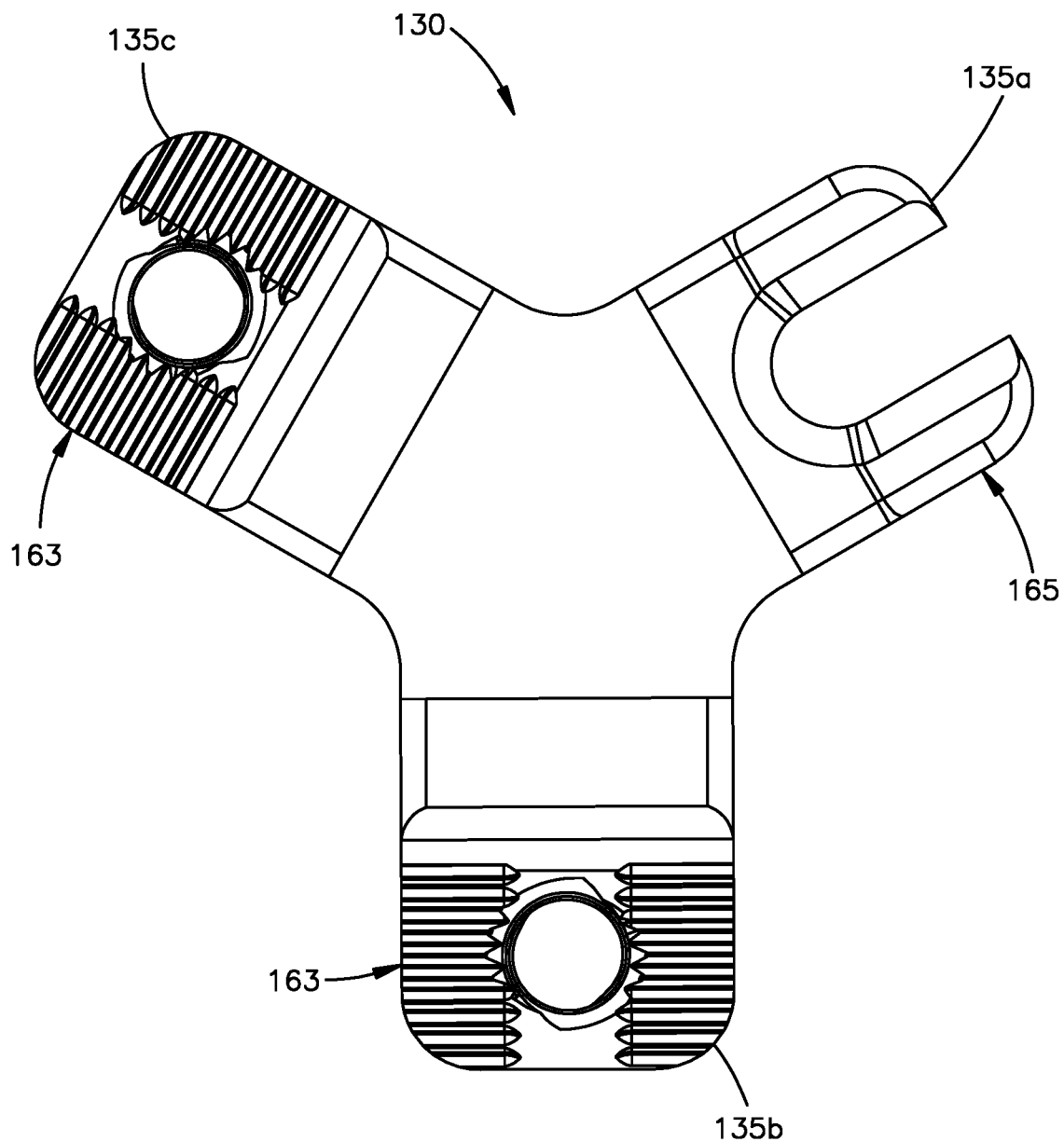
FIG. 14C is a top plan view of one of the first links of the linkage illustrated in FIG. 11, shown Y-shaped in accordance with an alternative embodiment.

Referring now to FIG. 14C, while the links 130 have been described as including first and second ends 135a and 135b, at least one of the links 130 can further include a third end 135c. Thus, the links 130 can be substantially "Y" shaped. Any one or more of the first, second, and third ends 135a, 135b, and 135c can include the first out-of-plane attachment end 163. Alternatively or additionally, any one or more of the of the first, second, and third ends 135a, 135b, and 135c can include the second out-of-plane attachment end 165. Thus, each of the first, second, and third ends 135a, 135b, and 135c can be configured to attach to another one of the links 130.

The embodiments described in connection with the illustrated embodiments have been presented by way of illustration, and the present invention is therefore not intended to be limited to the disclosed embodiments. Accordingly, those skilled in the art will realize that the invention is intended to encompass all modifications and alternative arrangements included within the spirit and scope of the invention, as set forth by the appended claims.

What is claimed:

1. A bone fixation linkage defining an inner end configured to face a bone to which the bone fixation linkage is configured to be attached, and an outer end opposite the inner end, the bone fixation linkage comprising:
   at least one first link that defines a threaded bone fixation aperture configured to receive a bone fixation member, wherein the first link defines first and second opposed attachment ends, each of the attachment ends defining plugs with external locking ribs, wherein the attachment ends are configured to be inserted into a complementary attachment ends of respective second links, such that the external locking ribs interfere with locking ribs of the second links to rotatably fix the first link and the second link to each other,
   wherein the aperture and the first and second attachment ends are aligned with each other along a straight central axis, and
   wherein the threaded bone fixation aperture is disposed between the first and second attachment ends, and is aligned with the first and second attachment ends along the straight central axis.

2. The bone fixation linkage of claim 1, wherein the first attachment end is an in-plane attachment end, and the second attachment end is an out-of-plane attachment end.

3. The bone fixation linkage of claim 1, wherein the first and second attachment ends are in-plane attachment ends.

4. The bone fixation linkage of claim 1, wherein the locking ribs of the first and second opposed attachment ends are spaced from each other along first and second planes, respectively, and the locking ribs prevent the first link from rotating with respect to the second links about respective axes of rotation that are normal to the first and second planes, respectively, when the first and second attachment ends are inserted into the complementary attachment ends of the respective second links.

5. The bone fixation linkage as recited in claim 1, wherein the locking ribs of the first and second opposed attachment ends are spaced from each other along respective arcuate paths.

6. The bone fixation linkage as recited in claim 1, further comprising the second links alternatingly arranged with the first link.

7. The bone fixation linkage of claim 1, wherein the locking ribs of the first attachment end are spaced from each other along a first plane, and the locking ribs of the second attachment end are spaced from each other about a second plane that is orthogonal to the first plane.

8. The bone fixation linkage of claim 1, wherein first link defines first and second opposed outermost ends that are outwardly spaced from the first and second attachment ends, respectively, along the straight central axis.

9. A bone fixation linkage defining an inner end configured to face a bone to which the bone fixation linkage is configured to be attached, and an outer end opposite the inner end, the bone fixation linkage comprising:
   at least one first link that defines first attachment end and a second attachment end opposite the first attachment end, and a body extending from the first attachment end to the second attachment end along a straight axis, wherein the first and second attachment ends are configured to be attached to attachment ends of respective second links, wherein the first attachment end is an in-plane attachment end so as to angulate in a first plane, and the second attachment end is an out-of-plane attachment end so as to angulate in a second plane that is orthogonal to the first plane.

10. The bone fixation linkage of claim 9, wherein the first link defines an aperture that extends through the body and is configured to receive a bone fixation member.

11. The bone fixation linkage of claim 9, wherein the first and second attachment ends define external locking ribs that are configured to interfere with locking ribs of the second links to rotatably fix the first link and the second link to each other.

12. The bone fixation linkage of claim 11, wherein the locking ribs of the first attachment end are spaced from each other along the first plane, and the locking ribs of the first attachment end are configured to prevent the respective second link from rotating with respect to the first link about an axis of rotation that is normal to the first plane.

13. The bone fixation linkage of claim 12, further comprising the second links.

14. The bone fixation linkage of claim 13, wherein the first and second attachment ends are first and second plug attachment ends, respectively, configured to be inserted into receptacles of the respective second links.

15. The bone fixation linkage as recited in claim 13, wherein each of the second links comprises a latch that is movable between a locked position that mates with the out-of-plane attachment end, and an unlocked position.

16. The bone fixation linkage as recited in claim 13, wherein the ribs of the first and second attachment ends are spaced from each other along respective convex paths, and the ribs of the second links are spaced from each other along a respective concave paths.

17. The bone fixation linkage of claim 12, wherein the locking ribs of the second attachment end are spaced from each other along the second plane, and the locking ribs of the second attachment end are configured to prevent the respective second link from rotating with respect to the first link about an axis of rotation that is normal to the second plane.

18. The bone fixation linkage as recited in claim 11, wherein the locking ribs of the first attachment end are spaced from each other along a first plane, and the locking ribs of the second attachment end are spaced from each other along a second plane that is orthogonal to the first plane.

19. The bone fixation linkage as recited in claim 11, wherein the locking ribs of the first attachment are arranged about a first central axis, and the locking ribs of the second attachment end are arranged about a second central axis that is perpendicular to the first central axis.

20. The bone fixation linkage as recited in claim 9, wherein the straight axis extends centrally through the first and second attachment ends.

* * * * *